US006758847B2

(12) United States Patent
Maguire

(10) Patent No.: US 6,758,847 B2
(45) Date of Patent: Jul. 6, 2004

(54) CIRCUMFERENTIAL ABLATION DEVICE ASSEMBLY AND METHODS OF USE AND MANUFACTURE PROVIDING AN ABLATIVE CIRCUMFERENTIAL BAND ALONG AN EXPANDABLE MEMBER

(75) Inventor: Mark A. Maguire, San Mateo, CA (US)

(73) Assignee: Atrionix, Inc., Palo Alto, CA (US)

( * ) Notice: Subject to any disclaimer, the term of this patent is extended or adjusted under 35 U.S.C. 154(b) by 33 days.

(21) Appl. No.: 10/164,538

(22) Filed: Jun. 6, 2002

(65) Prior Publication Data

US 2002/0198521 A1 Dec. 26, 2002

Related U.S. Application Data

(63) Continuation of application No. 09/435,283, filed on Nov. 5, 1999, now Pat. No. 6,500,174, which is a continuation-in-part of application No. 08/889,798, filed on Jul. 8, 1997, now Pat. No. 6,024,740.
(60) Provisional application No. 60/125,928, filed on Mar. 23, 1999, and provisional application No. 60/125,509, filed on Mar. 19, 1999.

(51) Int. Cl.$^7$ .............................. A61B 18/18; A61F 7/00
(52) U.S. Cl. .......................... 606/41; 607/101; 607/105
(58) Field of Search ........................ 606/41–50; 607/96, 607/98, 101–105, 113

(56) References Cited

U.S. PATENT DOCUMENTS 2,938,502 A    5/1960 Neal (List continued on next page.)

FOREIGN PATENT DOCUMENTS

EP            0823360 B1   2/1994

(List continued on next page.)

OTHER PUBLICATIONS

Avitall, et al., "Physics and Engineeringof Transcatheter Cardiac Tissue Ablation." JACC, vol. 22, No. 3, Sep. 1993.

(List continued on next page.)

*Primary Examiner*—Roy D. Gibson

(57) ABSTRACT

A medical balloon catheter assembly includes a balloon having a permeable region and a non-permeable region. The balloon is constructed at least in part from a fluid permeable tube such that the permeable region is formed from a porous material which allows a volume of pressurized fluid to pass from within a chamber formed by the balloon and into the permeable region sufficiently such that the fluid may be ablatively coupled to tissue engaged by the permeable region. The non-permeable region is adapted to substantially block the pressurized fluid from passing from within the chamber and outwardly from the balloon. The porous material may be a porous fluoropolymer, such as porous polytetrafluoroethylene, and the pores may be created by voids that are inherently formed between an interlocking node-fibril network that makes up the fluoropolymer. Such voids may be created according to one mode by expanding the fluoropolymer. The balloon may be formed such that the porous material extends along both the permeable and non-permeable regions. In one mode of this construction, the porous material is porous along the permeable region but is non-porous along the non-permeable region, such as for example by expanding only the permeable region in order to render sufficient voids in the node-fibril network to provide permeable pores in that section. The voids or pores in the porous material may also be provided along both permeable and non-permeable sections but are substantially blocked with an insulator material along the non-permeable section in order to prevent fluid from passing through. The insulator material may be dip coated, deposited, or extruded with the porous material in order to fill the voids. The insulator material may in one mode be provided along the entire working length of the balloon and then selectively removed along the permeable section, or may be selectively exposed to only the non-permeable sections in order to fill the voids or pores there.

12 Claims, 21 Drawing Sheets

U.S. PATENT DOCUMENTS

| | | |
|---|---|---|
| 3,781,781 A | 12/1973 | Groves, Jr. |
| 3,938,502 A | 2/1976 | Born |
| 4,117,836 A | 10/1978 | Erikson |
| 4,316,472 A | 2/1982 | Mirowski |
| 4,411,266 A | 10/1983 | Cosman |
| 4,441,286 A | 4/1984 | Cosman |
| 4,449,528 A | 5/1984 | Auth et al. |
| 4,522,205 A | 6/1985 | Taylor et al. |
| 4,569,801 A | 2/1986 | Molloy et al. |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III |
| 4,672,962 A | 6/1987 | Hershenson |
| 4,673,563 A | 6/1987 | Berne et al. |
| 4,676,258 A | 6/1987 | Inokuchi et al. |
| 4,699,147 A | 10/1987 | Chilson et al. |
| 4,757,820 A | 7/1988 | Itoh |
| 4,762,129 A | 8/1988 | Bonzel |
| 4,790,311 A | 12/1988 | Ruiz |
| 4,807,620 A | 2/1989 | Strul et al. |
| 4,841,977 A | 6/1989 | Griffith et al. |
| 4,882,777 A | 11/1989 | Narula |
| 4,898,591 A | 2/1990 | Jang et al. |
| 4,917,096 A | 4/1990 | Englehart et al. |
| 4,924,863 A | 5/1990 | Sterzer |
| 4,936,281 A | 6/1990 | Stasz |
| 4,940,064 A | 7/1990 | Desai |
| 4,945,912 A | 8/1990 | Langberg |
| 4,946,400 A | 8/1990 | Hall |
| 4,946,440 A | 8/1990 | Hall |
| 4,951,677 A | 8/1990 | Crowley et al. |
| 4,976,711 A | 12/1990 | Parins et al. |
| 4,998,933 A | 3/1991 | Eggers et al. |
| 5,000,185 A | 3/1991 | Yock |
| 5,002,059 A | 3/1991 | Crowley et al. |
| 5,035,694 A | 7/1991 | Kasprzyk et al. |
| 5,078,717 A | 1/1992 | Parins et al. |
| 5,078,736 A | 1/1992 | Behl |
| 5,090,958 A | 2/1992 | Sahota |
| 5,104,393 A | 4/1992 | Isner et al. |
| 5,131,397 A | 7/1992 | Crowley et al. |
| 5,147,355 A | 9/1992 | Friedman et al. |
| 5,156,157 A | 10/1992 | Valenta, Jr. et al. |
| 5,178,618 A | 1/1993 | Kandarpa |
| 5,190,540 A | 3/1993 | Lee |
| 5,195,990 A | 3/1993 | Weldon |
| 5,209,229 A | 5/1993 | Gilli |
| 5,222,501 A | 6/1993 | Ideker et al. |
| 5,226,430 A | 7/1993 | Spears et al. |
| 5,228,422 A | 7/1993 | Imran |
| 5,231,995 A | 8/1993 | Desai |
| 5,255,679 A | 10/1993 | Imran |
| 5,263,493 A | 11/1993 | Avitall |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards |
| 5,295,484 A | 3/1994 | Marcus et al. |
| 5,300,085 A | 4/1994 | Yock |
| 5,313,943 A | 5/1994 | Houser et al. |
| 5,324,255 A | 6/1994 | Passafaro et al. |
| 5,324,284 A | 6/1994 | Imram |
| 5,325,860 A | 7/1994 | Seward et al. |
| 5,331,966 A | 7/1994 | Bennett et al. |
| 5,342,292 A | 8/1994 | Nita et al. |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran et al. |
| 5,368,035 A | 11/1994 | Hamm et al. |
| 5,368,558 A | 11/1994 | Nita |
| 5,370,678 A | 12/1994 | Edwards et al. |
| 5,372,138 A | 12/1994 | Crowley et al. |
| 5,385,148 A | 1/1995 | Lesh |
| 5,385,544 A | 1/1995 | Edwards et al. |
| 5,391,197 A | 2/1995 | Burdette et al. |
| 5,409,000 A | 4/1995 | Imran |
| 5,411,524 A | 5/1995 | Rahul |
| 5,421,338 A | 6/1995 | Crowley et al. |
| 5,423,808 A | 6/1995 | Edwards et al. |
| 5,423,811 A | 6/1995 | Imran et al. |
| 5,427,119 A | 6/1995 | Swartz et al. |
| 5,433,708 A | 7/1995 | Nichols et al. |
| 5,437,664 A | 8/1995 | Cohen et al. |
| 5,447,509 A | 9/1995 | Mills et al. |
| 5,449,380 A | 9/1995 | Chin |
| 5,454,373 A | 10/1995 | Koger et al. |
| 5,456,682 A | 10/1995 | Edwards et al. |
| 5,458,568 A | 10/1995 | Racchini et al. |
| 5,465,716 A | 11/1995 | Avitall |
| 5,474,530 A | 12/1995 | Passafaro et al. |
| 5,484,400 A | 1/1996 | Edwards et al. |
| 5,487,385 A | 1/1996 | Avitall |
| 5,496,312 A | 3/1996 | Klicek |
| 5,496,346 A | 3/1996 | Horzewski et al. |
| 5,497,119 A | 3/1996 | Tedrow et al. |
| 5,497,774 A | 3/1996 | Swartz et al. |
| 5,501,227 A | 3/1996 | Yock |
| 5,505,702 A | 4/1996 | Arney |
| 5,505,730 A | 4/1996 | Edwards |
| 5,509,900 A | 4/1996 | Kirkman |
| 5,522,873 A | 6/1996 | Jackman et al. |
| 5,545,161 A | 8/1996 | Imran |
| 5,545,193 A | 8/1996 | Fleischman et al. |
| 5,549,661 A | 8/1996 | Kordis et al. |
| 5,558,672 A | 9/1996 | Edwards et al. |
| 5,562,720 A | 10/1996 | Stern et al. |
| 5,564,440 A | 10/1996 | Swartz et al. |
| 5,569,241 A | 10/1996 | Edwards |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,582,609 A | 12/1996 | Swanson et al. |
| 5,588,432 A | 12/1996 | Crowley |
| 5,606,974 A | 3/1997 | Castellano et al. |
| 5,607,422 A | 3/1997 | Smeets et al. |
| 5,617,854 A | 4/1997 | Munsif |
| 5,620,479 A | 4/1997 | Diederich |
| 5,630,837 A | 5/1997 | Crowley |
| 5,642,736 A | 7/1997 | Avitall |
| 5,645,082 A | 7/1997 | Sung et al. |
| 5,658,278 A | 8/1997 | Imran et al. |
| 5,673,695 A | 10/1997 | McGee et al. |
| 5,676,662 A | 10/1997 | Fleischhacker et al. |
| 5,683,445 A | 11/1997 | Swoyer |
| 5,685,322 A | 11/1997 | Sung et al. |
| 5,685,839 A | 11/1997 | Edwards et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |

| | | |
|---|---|---|
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Lamard |
| 5,722,401 A | 3/1998 | Pietroski et al. |
| 5,722,403 A | 3/1998 | McGee et al. |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |
| 5,730,127 A | 3/1998 | Avitall |
| 5,730,704 A | 3/1998 | Avitall |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,749,880 A | 5/1998 | Banas et al. |
| 5,753,358 A | 5/1998 | Korleski |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,766,750 A | 6/1998 | Korleski |
| 5,769,846 A | 6/1998 | Edwards et al. |
| 5,769,880 A * | 6/1998 | Truckai et al. ............... 607/101 |
| 5,779,698 A | 7/1998 | Clayman et al. |
| 5,782,239 A | 7/1998 | Webster, Jr. |
| RE35,880 E | 8/1998 | Waldman |
| 5,797,877 A | 8/1998 | Hamilton et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,807,249 A | 9/1998 | Qin et al. |
| 5,807,308 A | 9/1998 | Edwards |
| 5,807,391 A | 9/1998 | Wijkamp |
| 5,807,395 A | 9/1998 | Mulier et al. |
| 5,824,046 A | 10/1998 | Smith et al. |
| 5,836,874 A | 11/1998 | Swanson et al. |
| 5,846,218 A | 12/1998 | Brisken et al. |
| 5,851,232 A | 12/1998 | Lois |
| 5,891,135 A * | 4/1999 | Jackson et al. ............... 606/41 |
| 5,928,279 A | 7/1999 | Shannon et al. |
| 5,938,660 A | 8/1999 | Swartz et al. |
| 5,971,983 A | 10/1999 | Lesh |
| 6,012,457 A | 1/2000 | Lesh |
| 6,023,638 A | 2/2000 | Swanson |
| 6,024,739 A | 2/2000 | Ponzi |
| 6,024,740 A | 2/2000 | Lesh et al. |
| 6,027,779 A | 2/2000 | Campbell et al. |
| 6,064,902 A | 5/2000 | Haissaguerre et al. |
| 6,071,279 A | 6/2000 | Whayne et al. |
| 6,071,281 A | 6/2000 | Burnside et al. |
| 6,117,101 A | 9/2000 | Diederich et al. |
| 6,152,920 A | 11/2000 | Thompson et al. |
| 6,178,842 B1 | 1/2001 | Tachibana et al. |
| 6,210,356 B1 | 4/2001 | Anderson et al. |
| 6,241,754 B1 | 6/2001 | Swanson et al. |
| 6,251,109 B1 | 6/2001 | Hassett et al. |
| 6,305,378 B1 | 10/2001 | Lesh |

FOREIGN PATENT DOCUMENTS

| | | |
|---|---|---|
| WO | WO 93/00958 | 1/1993 |
| WO | WO 93/08755 | 5/1993 |
| WO | WO 93/16632 A1 | 9/1993 |
| WO | WO 93/20767 | 10/1993 |
| WO | WO 93/20770 | 10/1993 |
| WO | WO 93/20886 | 10/1993 |
| WO | WO 94/00050 | 1/1994 |
| WO | WO 94/21165 | 9/1994 |
| WO | WO 94/21167 | 9/1994 |
| WO | WO 94/21168 | 9/1994 |
| WO | WO 95/10318 | 4/1995 |
| WO | WO 95/10319 | 4/1995 |
| WO | WO 95/10321 | 4/1995 |
| WO | WO 95/19738 | 7/1995 |
| WO | WO 96/00036 | 1/1996 |
| WO | WO 96/00042 | 1/1996 |
| WO | WO 96/10961 | 4/1996 |
| WO | WO 96/26675 | 9/1996 |
| WO | WO 96/32885 | 10/1996 |
| WO | WO 96/32897 | 10/1996 |
| WO | WO 97/32525 | 9/1997 |
| WO | WO 97/37607 | 10/1997 |
| WO | WO 97/45156 | 12/1997 |
| WO | WO 98/02201 | 1/1998 |
| WO | WO 98/26724 | 6/1998 |
| WO | WO 98/49957 A1 | 11/1998 |
| WO | WO 99/00064 | 1/1999 |
| WO | WO 99/00066 A1 | 1/1999 |
| WO | WO 99/02096 A1 | 1/1999 |
| WO | WO 99/02096 | 1/1999 |
| WO | WO 00/07508 A1 | 2/2000 |

OTHER PUBLICATIONS

Cox, et al., "The Surgical Treatment of Atrial Fibrillation: I. Summary of the current concepts of the mechanisms of atrial flutter and atrial fibrillation," The Journal of Thoracic and Cardiovascular Surgery, pp. 402–405, 1991.

Cox, et al., "The surgical treatment of atrial fibrillation: IV Surgical Technique," The Journal Thoracic and Cardiovascular Surgery, pp. pp. 584–592, 1991.

Diederich, et al., Induction of Hyperthemia using an Intracavitary Multielement Ultrasonic Applicator, Transactions in Biomedical Engineering, vol. 36, No. 4 Apr. 1989.

Diederich, et. al. The Development of Intracavitary Ultrasonic Applicators for Hyperthermia: A Design and Experimental Study. Medical Physics, Jul./Aug. 1990.

Fram, et. al. feasibility of Radiofrequency Powered, Thermal Balloon Ablation of Atrioventricular Bypass Tracts Via the Coronary Sinus: In Vivo Canine Studies, Pace, vol. 18, pp. 1518–1530, Aug. 1995.

Haissaguerre et. al. "Right and Left Atrial Radiofrequency Catheter Therapy of Paroxysmal Atrial Fibrillation", Journalof Cardiovascular Electrophysiology, vol. 7, No. 12, pp. 1132–1144, Dec. 1996.

Hindricks, et. al., "IX Nonpharmacologic Management Catheter Ablation," Current Management of Arrythmias, pp. 373–378.

Jais, et. al., "Biatrial Dimensions Relevant to Catheter Ablation," NASPE 17th Annual Scientific Sessions Abstract Forum, Dec. 1995.

Jais, et. al., "A Focal Source of Atrial Fibrillation Treated by Discrete Radiofrequency Ablation," Circulation, vol. 95, No. 3 pp. 572–576, Feb. 4, 1997.

McMath, et. al., "Percutaneous Laser Balloon Coagulation of Accessory Pathways," Diagnostic and Therapeutic Cardiovascular Interventions, 1991.

Schuger, et. al., "Long Term Effects of Percutaneous Laser Balloon Ablation from the Canine Coronary Sinus," Circulation, vol. 86, No. 3, Sep. 1992.

Sueda, et. al., "Simple left atrial fibrillation associated with mitral valve diseases," Ann Thorac Surg 62:1796–1800 (1996).

* cited by examiner

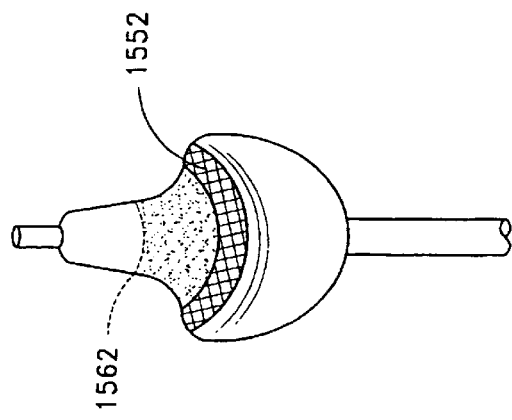
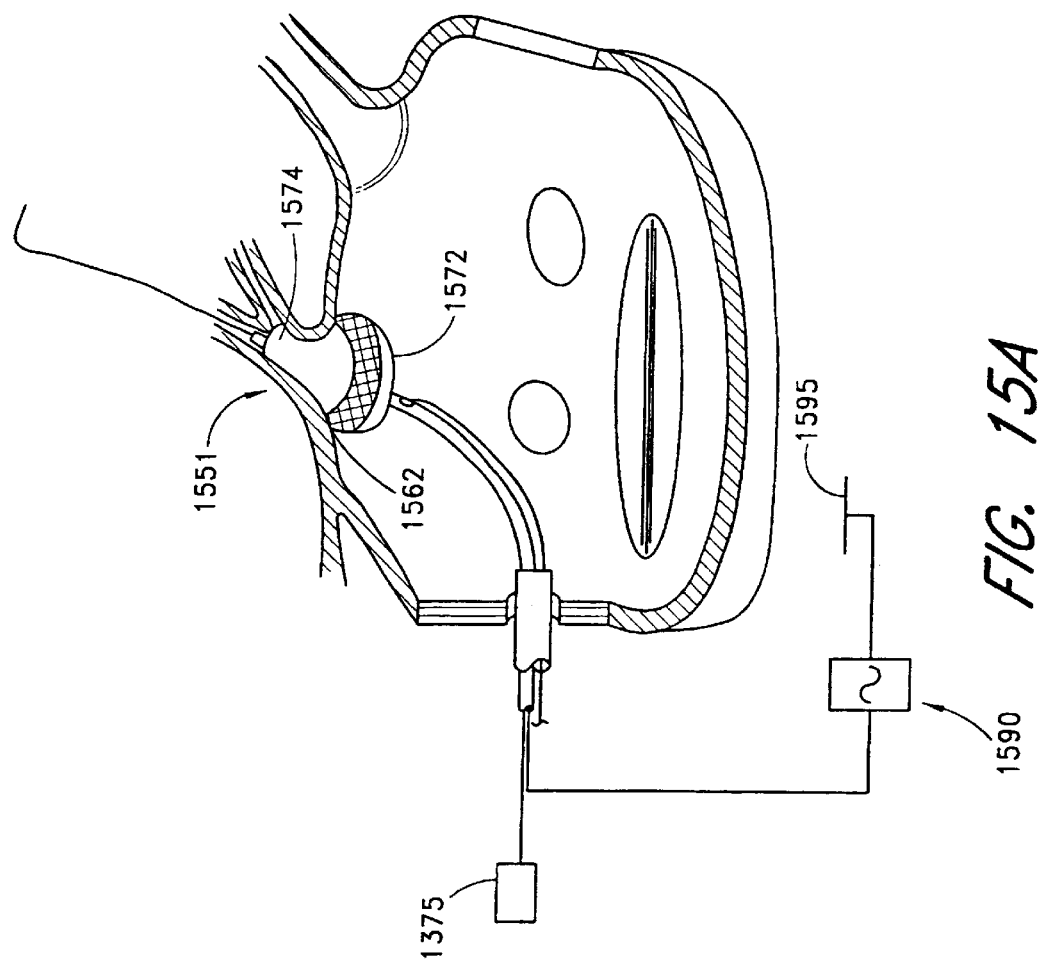

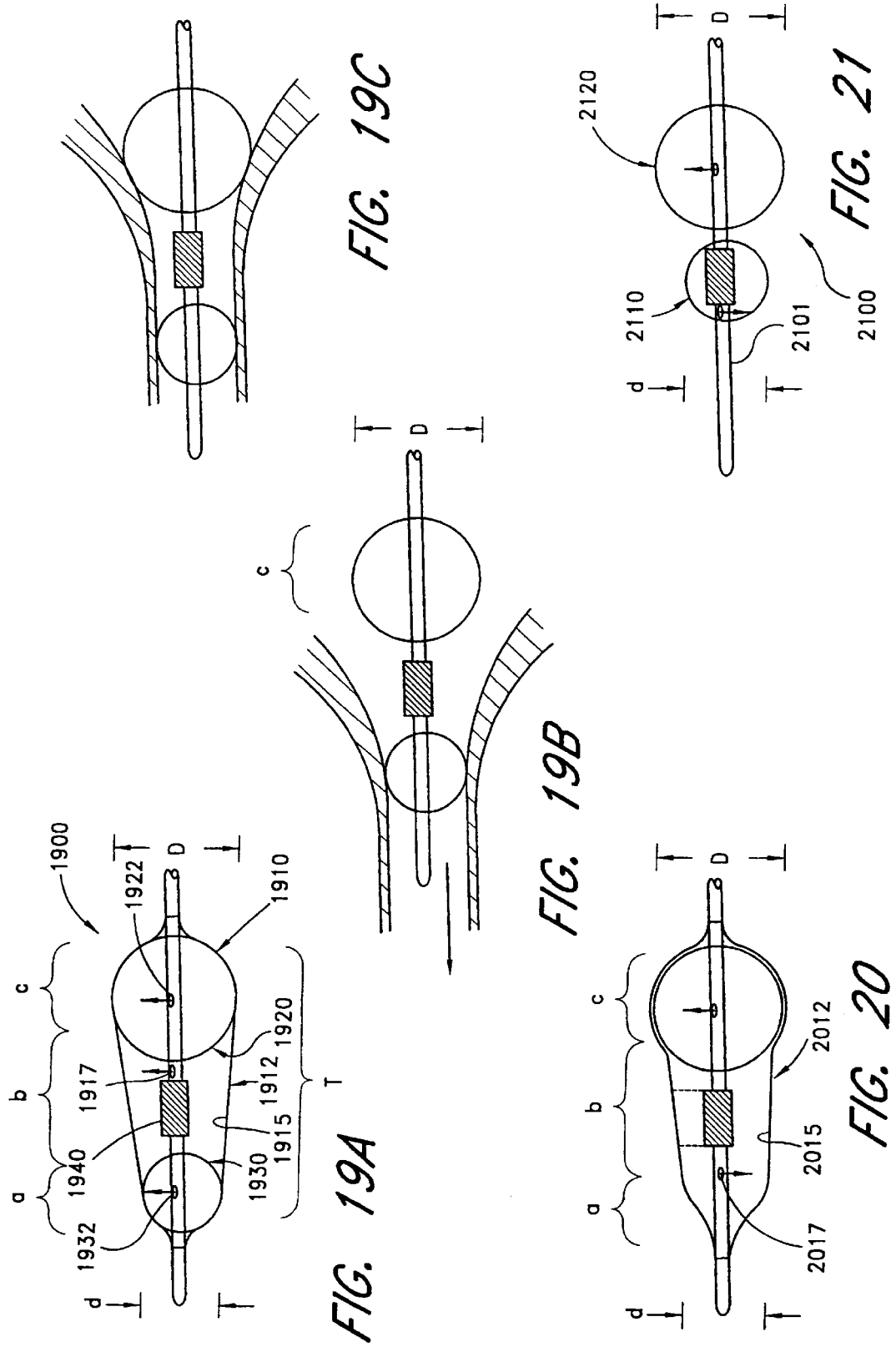

CIRCUMFERENTIAL ABLATION DEVICE ASSEMBLY AND METHODS OF USE AND MANUFACTURE PROVIDING AN ABLATIVE CIRCUMFERENTIAL BAND ALONG AN EXPANDABLE MEMBER

CROSS-REFERENCE TO RELATED APPLICATIONS

This application is a continuation application of U.S. patent application Ser. No. 09/435,283, filed Nov. 5, 1999, now issued as U.S. Pat. No. 6,500,174 on Dec. 31, 2002, which is a continuation-in-part of U.S. patent application Ser. No. 08/889,798, filed Jul. 8, 1997, now issued as U.S. Pat. No. 6,024,740 on Feb. 15, 2000. U.S. patent application Ser. No. 09/435,283 also claims the benefit of U.S. Provisional Application Serial No. 60/125,928, filed Mar. 23, 1999 and U.S. Provisional Application Serial No. 60/125,509, filed Mar. 19, 1999.

FIELD OF THE INVENTION

The present invention involves a surgical device and methods of manufacture and use. More specifically, it involves a circumferential ablation device assembly and associated methods of manufacture and use. One aspect of the present invention specifically involves an assembly and method incorporating a circumferential band along an intermediate region of an expandable member's working length for ablating a circumferential region of tissue engaged to the intermediate region at a location where a pulmonary vein extends from a left atrium.

BACKGROUND

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

Many local energy delivery devices and methods have been developed for treating the various abnormal tissue conditions in the body, and particularly for treating abnormal tissue along body space walls which define various body spaces in the body. For example, various devices have been disclosed with the primary purpose of treating or recanalizing atherosclerotic vessels with localized energy delivery. Several prior devices and methods combine energy delivery assemblies in combination with cardiovascular stent devices in order to locally deliver energy to tissue in order to maintain patency in diseased lumens such as blood vessels. Endometriosis, another abnormal wall tissue condition which is associated with the endometrial cavity and is characterized by dangerously proliferative uterine wall tissue along the surface of the endometrial cavity, has also been treated by local energy delivery devices and methods. Several other devices and methods have also been disclosed which use catheter-based heat sources for the intended purpose of inducing thrombosis and controlling hemorrhaging within certain body lumens such as vessels.

Detailed examples of local energy delivery devices and related procedures such as those of the types just described above are variously disclosed in the following references: U.S. Pat. Nos. 4,672,962 to Hershenson; U.S. Pat. Nos. 4,676,258 to InoKuchi et al.; U.S. Pat. No. 4,790,311 to Ruiz; 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stern et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa. The disclosures of these references are herein incorporated in their entirety by reference thereto.

Other prior devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism or in certain other known applications as a carrier or medium for the localized energy delivery, itself.

More detailed examples of ablation devices which use fluid to assist in electrically coupling electrodes to tissue are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al. To the extent not previously incorporated above, the disclosures of these references are herein incorporated in their entirety by reference thereto.

Atrial Fibrillation

Cardiac arrhythmias, and atrial fibrillation in particular, persist as common and dangerous medical ailments associated with abnormal cardiac chamber wall tissue, and has been observed especially in the aging population. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. Nos. 4,641,649 to Walinsky et al. and Published PCT Patent Application No. WO 96/32897 to Desai. The disclosures of these references are herein incorporated in their entirety by reference thereto.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, such as for example according to the disclosures of the following references: U.S. Pat. No. 4,673,563 to Beme et al.; U.S. Pat. No. 4,569,801 to Molloy et al.; and also "Current Management of Arrhythmias" (1991) by Hindricks, et al. However, such pharmacological solutions are not generally believed to be entirely effective in many cases, and are even believed in some cases to result in proarrhythmia and long term inefficacy. The disclosures of these references are herein incorporated in their entirety by reference thereto.

Several surgical approaches have also been developed with the intention of treating atrial fibrillation. One particular example is known as the "maze procedure," as is disclosed by Cox, J L et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996). The disclosure of these cited references are herein incorporated in their entirety by reference thereto.

The "maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins and to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "maze" procedure and its variations as reported by Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue that defines the atrial chambers. Some specifically disclosed approaches provide specific ablation elements that are linear over a defined length intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions, and include use of microwave, laser, ultrasound, thermal conduction, and more commonly, radiofrequency energies to create conduction blocks along the cardiac tissue wall.

Further more detailed examples of ablation device assemblies and methods for creating lesions along an atrial wall are disclosed in the following U.S. Patent references: U.S. Pat. No. 4,898,591 to Jang et al.; U.S. Pat. No. 5,104,393 to Isner et al.; U.S. Pat. No. 5,427,119; U.S. Pat. No. 5,487,385 to Avitall; U.S. Pat. No. 5,427,119 to Swartz et al.; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,575,766 to Swartz et al.; U.S. Pat. No. 5,582,609 to Swanson; U.S. Pat. No. 5,617,854 to Munsif; U.S. Pat. No 5,687,723 to Avitall; U.S. Pat. No. 5,702,438 to Avitall. To the extent not previously incorporated above, the disclosures of these references are herein incorporated in their entirety by reference thereto.

Other examples of such ablation devices and methods are disclosed in the following Published PCT Patent Applications: WO 93/20767 to Stern et al.; WO 94/21165 to Kordis et al.; WO 96/10961 to Fleischman et al.; WO 96/26675 to Klein et al.; and WO 97/37607 to Schaer. To the extent not previously incorporated above, the disclosures of these references are herein incorporated in their entirety by reference thereto.

Additional examples of such ablation devices and methods are disclosed in the following published articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996). The disclosures of these references are herein incorporated in their entirety by reference thereto.

In addition to those known assemblies just summarized above, additional tissue ablation device assemblies have also been recently developed for the specific purpose of ensuring firm contact and consistent positioning of a linear ablation element along a length of tissue by anchoring the element at least at one predetermined location along that length, such as in order to form a "maze"-type lesion pattern in the left atrium. One example of such assemblies includes an anchor at each of two ends of a linear ablation element in order to secure those ends to each of two predetermined locations along a left atrial wall, such as at two adjacent pulmonary veins, so that tissue may be ablated along the length of tissue extending therebetween.

In addition to attempting atrial wall segmentation with long linear lesions for treating atrial arrhythmia, other ablation device and method have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome —various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995); "Long-term effects of percutaneous laser balloon ablation from the canine coronary sinus", Schuger C D et al., *Circulation* (1992) 86:947–954; and "Percutaneous laser balloon coagulation of accessory pathways", McMath L P et al., *Diagn Ther Cardiovasc Interven* 1991; 1425:165–171. The disclosures of these references are herein incorporated in their entirety by reference thereto.

Arrhythmias Originating from Foci in Pulmonary Veins

Various modes of atrial fibrillation have also been observed to be focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the inappropriate arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996) (previously incorporated by reference above). Haissaguerre, et al. discloses radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radiofrequency ablation," *Circulation* 95:572–576 (1997). The disclosure of this reference is herein incorporated in its entirety by reference thereto. Jais et al. discloses treating patients with paroxysmal arrhythmias originating from a focal source by ablating that source. At the site of arrhythmogenic tissue, in both right and left atria, several pulses of a discrete source of radiofrequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed in Published PCT Patent Application No. WO 99/02096 to Diederich et al., and also in the following U.S. Patents and patent applications: U.S. Pat. No. 6,024,740 for "Circumferential Ablation Device Assembly" to Michael D. Lesh et al., issued Feb. 15, 2000; U.S. Pat. No. 6,012,457 for "Device and Method for Forming a Circumferential Conduction Block in a Pulmonary Vein" to Michael D. Lesh, issued Jan. 11, 2000; U.S. Pat. No. 6,117,101 "Circumferential Ablation Device Assembly" to Chris J. Diederich et al., issued Sep. 12, 2000; and U.S. Ser. No. 09/260,316 for "Device and Method for Forming a Circumferential Conduction Block in a Pulmonary Vein" to Michael D. Lesh.

Another specific device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 and a related Published PCT Patent Application No. WO 99/00064. The disclosures of these references are herein incorporated in their entirety by reference thereto.

SUMMARY OF THE INVENTION

It is an object of the invention to provide a circumferential ablation device assembly, and related method of manufacture and use, which ablates a circumferential region of tissue at a location where a pulmonary vein extends from an atrium by ablatively coupling an ablative fluid medium within an expandable member to the circumferential region of tissue across a circumferential band which circumscribes an intermediate region of the expandable member and engages the circumferential region of tissue when the expandable member is expanded.

It is another object of the invention to provide such a circumferential ablation device assembly, and related methods of use and manufacture, wherein the intermediate region of the expandable member's working length is constructed at least in part of a porous fluoropolymer material.

It is a further object of the invention to provide such an expandable member with the porous fluoropolymer material along the intermediate region and also with first and second end portions of the working length that do not include a fluoropolymer.

It is another object of the invention to provide a circumferential ablation device assembly, and related methods of manufacture and use, which ablatively couples an ablation element to only a region of tissue engaged to an intermediate region between two end portions along a working length of an expandable member.

It is another object of the invention to provide a medical device assembly which ablatively couples an ablative fluid medium from within an expandable member to only a region of tissue engaged to only a fluid permeable section along the working length of the expandable member.

It is a further object of the invention to provide a circumferential ablation device assembly, and related methods of use and manufacture, that includes a balloon with elastomeric first and second end portions along its working length and also with a fluid permeable circumferential band circumscribing an intermediate region between those end portions.

It is a further object of the invention to provide a circumferential ablation device assembly, and related methods of use and manufacture, that includes a balloon having a fluid permeable fluoropolymer that is integral along the balloon's working length and includes an insulator on each of two end portions of the working length such that only a circumferential band circumscribing an intermediate region between the end portions is left permeable. It is a further object to provide such a balloon with the two end portions impregnated with a filler as fluid insulation.

It is a further object of the invention to provide a circumferential ablation device assembly, and related methods of use and manufacture, that includes an expandable member having a working length constructed of an elastomeric wall that is constructed to be fluid permeable along only a circumferential band which circumscribes an intermediate region located between two end portions of the working length.

It is a further object of the invention to provide a circumferential ablation device assembly, and related methods of use and manufacture, that includes a balloon with a fluoropolymeric material that is integral along the balloon's working length while only an intermediate region between two end portions of the working length is fluid permeable to allow for ablative coupling of an ablation medium across the fluoropolymeric material.

It is a further object of the invention to provide a circumferential ablation device assembly, and related methods of use and manufacture, that includes a balloon having a working length with relatively elastic first and second end portions and a relatively inelastic intermediate region between the first and second end portions, and which ablates only a circumferential region of tissue surrounding the intermediate region when the balloon is inflated.

It is a further object of the invention to provide a medical device catheter having a balloon with a working length that has a porous fluoropolymeric permeable section and also an elastomeric section.

It is a further object of the invention to provide such a catheter where the permeable fluoropolymer section is between two elastomeric end portions of the working length.

It is a further object of the invention to provide a circumferential ablation member with an expandable member having a taper along the working length and also with an ablation element coupled to a circumferential area surrounding the taper along the working length.

It is also a further object of the invention to provide a circumferential ablation member which an expandable member that is adapted to seat at a pulmonary vein ostium such that an ablation circumferential band surrounding the working length is aligned with and ablates a region of tissue along the ostium.

It is a further object of the invention to provide a circumferential ablation member for ablating a circumferential region of tissue along a pulmonary vein ostium and which includes an expandable member with a working length having two end portions that have larger outer diameters than an intermediate region of the working length that includes an ablative circumferential band which is adapted to seat at the pulmonary vein ostium.

Other objects of the invention are contemplated which would be apparent to one of ordinary skill based upon the totality of this disclosure, including without limitation the following summary of various modes, aspects, features, and variations of the particular embodiments.

In one mode of the invention, a circumferential ablation device assembly includes an elongate body with a circumferential ablation member along its distal end portion having an expandable member. The expandable member is located along the distal end portion of the elongate body, and is expandable along a working length which encloses at least in part a fluid chamber that is adapted to fluidly couple to a pressurizeable source of fluid. The working length also has first and second end portions and an intermediate region extending between the end portions. The end portions are substantially non-permeable to fluid, whereas the intermediate region is fluid permeable. With the working length expanded to a radially expanded condition, the intermediate region has an expanded outer diameter that is adapted to radially engage the circumferential region of tissue. The working length is thus adapted to allow fluid to pass from within the fluid chamber and outwardly into the permeable section of the intermediate region where it may be ablatively coupled to the engaged circumferential region of tissue.

In one aspect of this mode, the circumferential ablation member includes an ablation electrode element that is constructed to electrically couple to a volume of pressurized electrically conductive fluid passing from within the fluid chamber and into the permeable section of the intermediate region of the working length. Accordingly, current from the electrode element flows through the electrically conductive fluid and outwardly from the ablation member only through the permeable section along the intermediate region and into the circumferential region of tissue for ablation there.

In another aspect of this mode, the permeable section is constructed from a substantially non-permeable material that has a plurality of apertures formed therethrough which form pores to render that section permeable, whereas in another aspect the permeable section is instead constructed from an inherently porous material with the permeability arising from a plurality of pores that are integral to the porous material.

In another aspect of this mode, the permeable section comprises a porous fluoropolymer material, and may be more particularly a porous polytetrafluoroethylene material.

In another aspect of this mode, the expandable member is an inflatable balloon. The balloon is inflatable with pressurized fluid in order to expand from the radially collapsed condition to the radially expanded condition.

In one particular beneficial construction, the balloon along the intermediate region is constructed at least in part from a porous fluoropolymer material which forms the permeable section, and along the first and second end portions the balloon is constructed at least in part from an elastomer.

In another aspect of this mode, the permeable section forms a circumferential band that circumscribes the working length along the intermediate region. In one particular variation of this aspect, the circumferential band has a band length relative to the longitudinal axis and which is substantially shorter than the working length, and may be less than two-thirds the working length or even one-half of the working length.

In another aspect of this mode, the working length has a proximal end and a distal end and also has a tapered shape with a distally reducing outer diameter from the proximal end to the distal end. In one more particular beneficial variation, the tapered shape is "pear"-shaped and has a contoured surface between the proximal end and the distal end with a relatively "forward" or "distal"-looking face along the contoured surface adjacent the proximal end. Further to this variation, the permeable section is provided along a distally-looking face and is adapted to be advanced distally against a circumferential region of tissue when expanded, such as in order to ablate a region of tissue along a posterior left atrial wall which surrounds a pulmonary vein ostium and isolates the associated vein from a substantial portion of the left atrium.

Another mode of the invention provides a medical catheter assembly with a balloon positioned along a distal end portion of an elongate body which ablatively couples an ablation element to tissue via an ablative medium provided by a fluid along a fluid permeable portion of the balloon. The balloon defines a fluid chamber and has a working length that is expandable with a volume of pressurized fluid from a radially collapsed condition having a radially collapsed profile to a radially expanded condition having a radially expanded profile which is larger than the radially collapsed profile. The working length further includes a non-permeable section and a permeable section. The non-permeable section is constructed to substantially prevent the pressurized fluid from passing from within the fluid chamber and outwardly through and from the balloon in the radially expanded condition. The permeable section is constructed at least in part of a porous material having a plurality of pores. In the radially expanded condition the pores are constructed to substantially allow the pressurized fluid to pass from within the enclosed chamber and outwardly from the balloon through the permeable section.

In one aspect of this mode, the porous material is constructed at least in part from a porous fluoropolymer material and the plurality of pores are integrally formed in the porous fluoropolymer material.

In one beneficial variation of this aspect, the porous fluoropolymer material includes a porous polytetrafluoroethylene material. The pores according to this variation may be formed by and between a plurality of nodes which are interconnected by a plurality of fibrils that make up the polytetrafluoroethylene material, and may be located along a length of the porous polytetrafluoroethylene material which extends along both the non-permeable and permeable sections.

According to the polytetrafluoroethylene embodiment providing the pores along both the permeable and non-permeable sections, the pores along the non-permeable section are substantially blocked and non-permeable to the pressurized fluid within the fluid chamber and the pores along the permeable section are substantially open and permeable to pressurized fluid within the fluid chamber. Further to this embodiment, the pores along the non-permeable section may be blocked with an insulator material, which may be a polymer, or more specifically an elastomer in order to provide the working length of the balloon elastomeric qualities during in vivo use. In further embodiments, the insulator material may be a deposited material, such as plasma deposited materials, vapor deposited materials, ion beam deposited materials, or sputter coated materials, or may be a dip-coated material, or may be a thermoplastic material which is melted to the porous polytetrafluoroethylene material along the non-permeable section. In still further embodiments, the insulator material may be a coating over the outer surface of the porous polytetrafluoroethylene, such as a tubular material that may be an elastomer which is coaxially disposed relative to the non-permeable section, or may be a filler material within the pores along the non-permeable section.

In one specific beneficial variation, the porous polytetrafluoroethylene material is formed in a porous tube which is relatively non-compliant, and the tubular material further comprises an elastomer which is relatively compliant, such that the balloon in the radially collapsed condition is characterized by the porous polytetrafluoroethylene material in a folded condition and also by the tubular material in a relatively non-stretched condition, and the balloon in the radially expanded condition is characterized by the porous polytetrafluoroethylene material in an unfolded condition and also by the tubular material in a radially stretched condition.

In another variation of the porous polytetrafluoroethylene aspect, the porous material is formed from a tape which is oriented in a helical pattern with adjacent windings which are fused to form a continuous porous tube that defines at least in part the fluid chamber.

In another aspect of this mode, the working length is constructed at least in part from a polytetrafluoroethylene material having a length that extends along both the non-permeable and permeable sections. The polytetrafluoroethylene material according to this aspect is substantially non-porous along the non-permeable section, and is porous along the permeable section to thereby form the porous material.

In one variation of this aspect, the polytetrafluoroethylene material along the non-permeable section includes a plurality of non-permeable pores. The non-permeable pores are sufficiently small to prevent passage of the pressurized fluid from within the fluid chamber and outwardly from the balloon through the non-permeable section, and the polytetrafluoroethylene material along that section is therefore effectively non-porous. In a further more detailed embodiment of this variation, the plurality of pores along the permeable section are formed by and between a first plurality of nodes which are interconnected by a first plurality of fibrils, whereas the plurality of non-permeable pores are formed by and between a second plurality of nodes and interconnecting fibrils.

In another variation of the polytetrafluoroethylene material aspect, the material is expanded from a cured state along the permeable section and is relatively un-expanded and substantially in the cured state along the non-permeable section, such as for example being stretched and unstretched in the permeable and non-permeable sections, respectively.

In another aspect of this mode, the working length includes first and second end portions with an intermediate region extending therebetween. The first end portion includes the non-permeable section, the intermediate region includes the permeable section, and the second end portion includes a second non-permeable section of similar construction to the first non-permeable section.

In one beneficial variation of this aspect, the permeable section forms a circumferential band that circumscribes the working length along the intermediate region. In the radially expanded condition the intermediate region is constructed to radially engage a circumferential region of tissue along a body space wall of a body space, whereas the first and second end portions are further constructed to radially engage first and second adjacent regions of tissue, respectively, on opposite sides of the circumferential region of tissue. The permeable section is adapted to allow a volume of electrically conductive fluid to pass from within the fluid chamber and outwardly from the balloon through the pores. The assembly according to this beneficial variation further includes an ablation electrode that is constructed to electrically couple with the electrically conductive fluid within the fluid chamber and therefore to the circumferential region of tissue as the electrically conductive fluid flows outwardly from the balloon through the permeable section. According to this beneficial assembly, the electrical coupling from the ablation electrode and through the volume of electrically conductive fluid passing through the permeable section is substantially isolated to the circumferential region of tissue engaged by the intermediate region and is substantially shielded from the adjacent regions of tissue by the first and second end portions.

In another aspect of this mode, the non-permeable and permeable sections are located longitudinally adjacent each other along the working length relative to the longitudinal axis, and in one particular variation the permeable section is located distally adjacent the non-permeable section.

In another aspect of this mode, the working length has a proximal section and a distal section and a tapered shape with a distally reducing outer diameter from the proximal section to the distal section, and the permeable section is located along the tapered region. In one particular variation of this aspect, the permeable section forms a circumferential band that circumscribes the working length along the taper.

In another aspect of this mode, the permeable section is further constructed to allow a volume of electrically conductive fluid to pass from within the fluid chamber and outwardly through and from the balloon through the pores, and the assembly further includes an ablation electrode which is constructed to electrically couple to the volume of electrically conductive fluid within the fluid chamber.

Another mode of the invention is a method for forming a medical balloon catheter device assembly that is adapted to deliver a volume of fluid to a region of tissue in a body. This method includes constructing a fluid permeable tube having a permeable section formed at least in part from a porous material. This construction uses a porous material having a plurality of pores which are adapted to allow a volume of pressurized fluid to pass from within and outwardly through the tube, and further results in a tubular construction having a non-permeable section which is adapted to substantially prevent the volume of pressurized fluid from passing from within and outwardly through the tube. This method further includes securing the fluid permeable tube to a distal end portion of an elongate catheter body in order to form a balloon which defines a pressurizeable fluid chamber over the catheter body and which includes a working length that is adapted to radially expand from a radially collapsed condition to a radially expanded condition when the fluid chamber is filled with the pressurized fluid. The method also includes coupling the pressurizeable fluid chamber with a distal port of a fluid passageway that extends along the catheter body between the distal port and a proximal port along the proximal end portion of the elongate catheter body which is adapted to couple to a pressurizeable fluid source, and also includes positioning the permeable section along the working length.

One aspect of this method mode further includes forming a taper along the working length of the balloon having a distally reducing outer diameter, and positioning the permeable section along the taper. The non-permeable section may also be positioned along the taper.

Another aspect of this method includes constructing the fluid permeable tube at least in part from a porous fluoropolymer having a plurality of voids that form the pores.

One variation of this aspect also includes constructing the porous fluoropolymer to include a plurality of nodes which are interconnected with fibrils to form a node-fibril network such that the plurality of voids are formed between the nodes and interconnecting fibrils.

Another aspect of this method mode includes constructing an ablation electrode to electrically couple to an electrical current source and also to the permeable section when the pressurizeable fluid chamber is filled with an electrically conductive fluid.

One variation of this aspect further includes securing the ablation electrode to the distal end portion of the elongate catheter body, and securing the fluid permeable tube to the elongate catheter body on opposite sides of the ablation electrode such that the ablation electrode is positioned within the fluid chamber.

Another aspect of this method mode includes constructing the fluid permeable tube such that both the permeable and non-permeable sections are formed at least in part from the porous material.

One variation of this aspect includes forming the fluid permeable tube such that the plurality of pores are provided along both the permeable and the non-permeable sections, and substantially blocking the pores along the non-permeable section such that the blocked pores are substantially non-permeable to the volume of fluid when the fluid is pressurized.

One more particular embodiment of this variation includes blocking the pores along the non-permeable section with an insulator material, such as by dip coating the non-permeable section with the insulator material, melting the insulator material to the non-permeable section, or depositing the insulator material along the non-permeable section.

Another more particular embodiment of the insulating variation includes substantially blocking the pores along both the permeable section and the non-permeable section with the insulator material, and then selectively removing the insulator material such that the pores along the permeable section are left open and un-blocked and the pores along the non-permeable section are left blocked. The insulation may be selectively removed in one beneficial method by dissolving the insulator material along the permeable section with a solvent, which process may further include selectively masking the insulator material along the non-permeable section from being exposed to and dissolved by the solvent.

Another mode of the invention includes a method for treating a region of tissue within a body by expanding a balloon from a radially collapsed condition to a radially expanded condition with a volume of pressurized fluid within a fluid chamber defined at least in part by the balloon, forcing the pressurized fluid from within the fluid chamber and outwardly from the balloon through a plurality of pores provided along a permeable section of the balloon, and substantially blocking the pressurized fluid from passing outwardly from and through the balloon along a non-permeable section of the balloon.

One aspect of this method further includes engaging the permeable section with a region of tissue and then forcing the pressurized fluid outwardly from the balloon through the pores along the permeable section and into the region of tissue. Further to this aspect, the pressurized fluid is forced outwardly from the balloon through the permeable section by weeping the fluid into the region of tissue without forming pressurized jets of fluid into the region of tissue.

Another aspect of this method includes engaging the permeable section with a circumferential region of tissue along a body space wall which defines at least in part a body space, and then forcing the pressurized fluid outwardly from the balloon through the pores along the permeable section and in a circumferential pattern into the circumferential region of tissue. One beneficial variation of this aspect of the method includes engaging the permeable section with a circumferential region of tissue along a pulmonary vein or with a circumferential region of tissue that surrounds a pulmonary vein ostium along a posterior left atrial wall. Another beneficial variation includes electrically coupling an ablation electrode to the pressurized fluid which is an electrically conductive fluid, and ablating the circumferential region of tissue with the pressurized fluid as it passes outwardly form the balloon through the permeable section and into the circumferential region of tissue. Further to this variation, the fluid may be passed to the circumferential region of tissue while substantially shielding the adjacent regions of tissue from electrically coupling to the ablation electrode via the pressurized fluid as it passes outwardly from the balloon through the permeable section and into the circumferential region of tissue. A further more detailed embodiment of this shielding variation includes radially engaging the non-permeable section with an adjacent region of tissue adjacent to the circumferential region of tissue engaged with the permeable section. This more detailed embodiment of the method may further include radially engaging a second non-permeable section with a second adjacent region of tissue that is adjacent to the circumferential region of tissue opposite the first adjacent region of tissue.

Another mode of the invention provides a circumferential ablation member with an expandable member constructed of two expandable elements along each of two end portions of the expandable member and a tubular member extending between the expandable elements which includes a circumferential band that is fluid permeable, wherein a fluid chamber is formed by the expandable elements and the tubular member extending therebetween, and such that fluid from the fluid chamber may be ablatively coupled to a circumferential region of tissue engaged by the circumferential band.

In one aspect of this mode, an electrode is adapted to be electrically coupled to the fluid within the chamber and thus to tissue engaged by the permeable circumferential band. In one variation of this aspect, the electrode is provided along an internal catheter shaft extending between the expandable elements.

In another mode, a medical catheter assembly has an expandable member that encloses a fluid chamber and also an inner expansion element such that the expansion element is adapted to expand a first portion of the expandable member's working length to a different outer diameter than a second portion of the working length.

In one aspect of this mode, the working length of the expandable member further comprises a circumferential band that is permeable to the fluid within the fluid chamber.

In another aspect of this mode, the expandable member encloses first and second inner expansion elements. A tubular wall extends between those outer surfaces to enclose the fluid chamber. The working length of the expandable member includes an intermediate region constructed of the tubular wall, and also first and second end portions on opposite sides of the intermediate region, wherein the first and second inner expansion elements are located along the first and second end portions.

In a further variation of this aspect, the inner expansion elements are adapted to expand to different outer diameters such that the working length is tapered between the first and second end portions, and more particularly in one variation so that the working length has a distally reducing outer diameter.

In another mode, a circumferential ablation device assembly and method provide an elongate body with a circumferential ablation member on the distal end portion that includes a first expandable member, and a second expandable member is further provided along the distal end portion in a longitudinally spaced location relative to the first expandable member. An ablation element cooperates with at least one of the first and second expandable members in order to ablatively couple to tissue engaged therewith in the expanded condition. In one particular aspect of this mode, the ablation element cooperates with the first expandable member, which is distal to the second expandable member on the distal end portion, and ablatively couples to tissue engaged by the first expandable member.

BRIEF DESCRIPTION OF THE DRAWINGS

FIGS. 1A–E shows schematic views of different types of circumferential patterns according to the invention.

FIG. 15A shows one mode of using another circumferential ablation device according to the present invention in order to ablate a circumferential region of tissue along an atrial wall and surrounding a pulmonary vein ostium.

FIG. 15B shows a perspective view of a circumferential ablation member for use according to the ablation device shown in FIG. 15A, and shows a "pear"-shaped balloon with an ablative circumferential band located at least in part along a "distal-looking" face along a contoured taper of the balloon.

FIG. 19A shows a circumferential ablation member of the invention which includes a tapered expandable member with two inner expansion elements and a tubular wall extending therebetween to form an inner fluid chamber that is adapted to ablatively couple to tissue engaged along the tubular wall.

FIGS. 19B–C shows the circumferential ablation member shown in FIG. 19A in sequential modes of use for positioning the circumferential ablation member at a desired location for ablatively coupling an ablation element within the expandable member to tissue at a location where a pulmonary vein extends from an atrium.

FIG. 20 shows a circumferential ablation member of the invention which includes a tapered expandable member with an outer skin that encloses one inner expansion element for expanding a portion of the working length of the outer skin to a larger outer diameter than another portion of the working length.

FIG. 21 shows a circumferential ablation member on the distal end of a catheter with a first expandable member and a second expandable member and an ablation element within the first expandable member.

DETAILED DESCRIPTION OF PARTICULAR EMBODIMENTS

Particular Definitions

Various terms are defined throughout this specification, and the meaning of any particular term is to be understood in the context of this entire document, in addition to the context of a particular description or use given in a specific circumstance as described hereunder. Various of such terms are to be understood as follows:

The terms "circumference" or "circumferential", including derivatives thereof, are herein intended to mean a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be, for example, circular, oblong, ovular, elliptical, or otherwise planar enclosures. A circumferential path may also be three dimensional, such as, for example, two opposite-facing semi-circular paths in two different parallel or off-axis planes that are connected at their ends by line segments bridging between the planes.

Figure 1E:
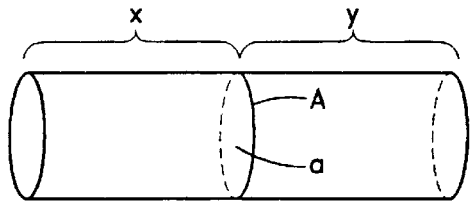
Figure 1E:
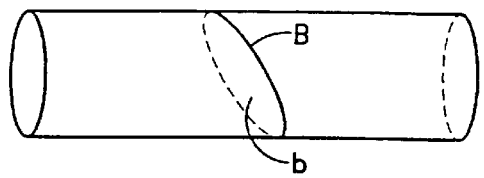
Figure 1E:
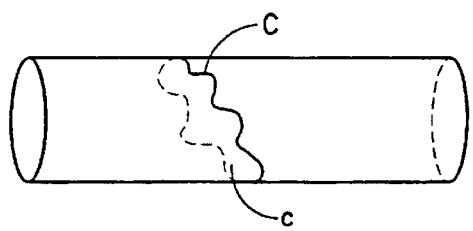
Figure 1E:
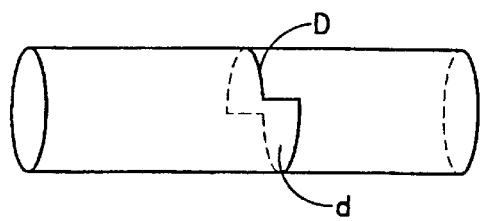
Figure 1E:
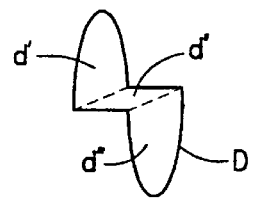

For purpose of further illustration, FIGS. 1A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 1D, FIG. 1E shows an exploded perspective view of circumferential path D as it circumscribes multiplanar portions of the pulmonary vein lumen shown at d', d", and d''', which together make up region d as shown in FIG. 1D.

The term "transect", including derivatives thereof, is also herein intended to mean to divide or separate a region of space into isolated regions. Thus, each of the regions circumscribed by the circumferential paths shown in FIGS. 1A–D transects the respective pulmonary vein, including its lumen and its wall, to the extent that the respective pulmonary vein is divided into a first longitudinal region located on one side of the transecting region, shown, for example, at region "X" in FIG. 1A, and a second longitudinal region on the other side of the transecting plane, shown, for example, at region "Y" also in FIG. 1A.

Therefore, a "circumferential conduction block" according to the present invention is formed along a region of tissue which follows a circumferential path, such as along the pulmonary vein wall and circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element", including derivatives thereof, is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type that is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoablation element adapted to sufficiently cool tissue to substantially alter the structure thereof may be suitable if adapted according to the teachings of the current invention.

Furthermore, a fluid ablation element, such as a wall that is porous or has a discrete port (or a plurality of ports) which is fluidly coupled to a fluid delivery source, may be adapted to couple an ablation medium to the tissue for ablation. In one aspect, the fluid ablation element may infuse the ablation medium, such as a fluid containing alcohol, directly into the tissue adjacent to the wall in order to substantially alter the nature of that tissue. In another aspect, the fluid ablation element may supply radiofrequency or other mode of electrical current to the tissue by electrically coupling an electrical ablation element to the tissue via an ablation medium which is an electrically conductive fluid, such as for example an ionic fluid which may be, in one illustrative variation, hypertonic saline. Moreover, the terms "ablation medium" are intended to mean a medium that cooperates with one or more of the assemblies herein described in order to directly couple to and ablate the intended tissue.

The terms "porous" or "permeable", including derivatives thereof, are herein used interchangeably and are intended to mean a material wall construction having sufficient void volume to allow a substance to permeate into and across the wall, including allowing for such substrate to elude through and out from the wall, such as by weeping or in fluid jets, or by merely "absorbing" the substrate into the void volume in the wall wherein substantial flow of the substrate completely through and from the wall is substantially limited or even prevented. Examples of "porous" or "permeable" materials for the purpose of illustration include without limitation: a material wall with inherent void volume upon formation of the wall; a material wall that is not inherently porous but with apertures formed therethrough such as for example by mechanical drilling or laser/optical drilling; and a material wall with chemically formed void volume.

Design, Manufacture, and Use of Particular Embodiments

Figure 2:
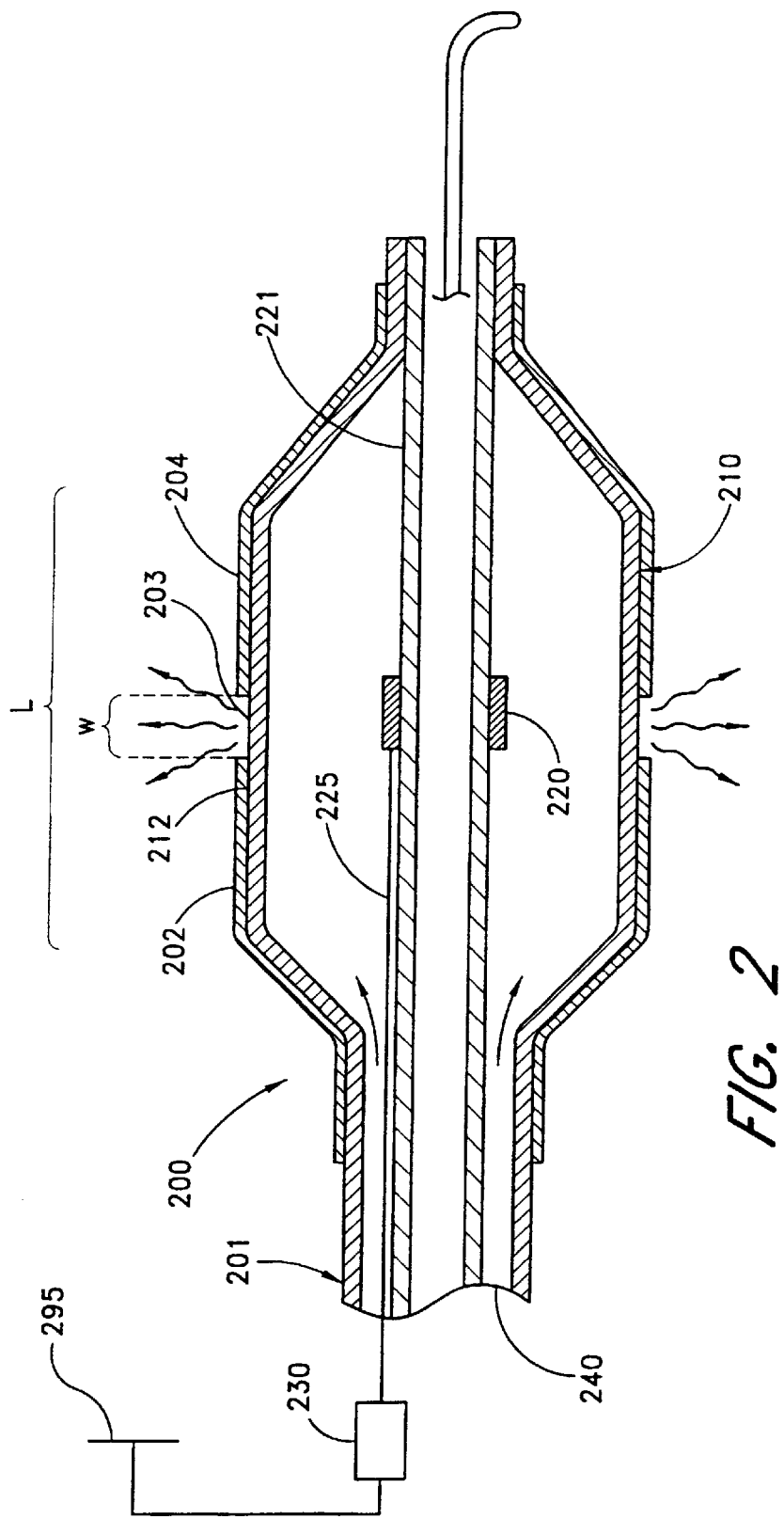
FIG. 2 shows a longitudinal cross-sectional view of one type of circumferential ablation device with a balloon ablation member that is secured to the distal end of an over-the-wire catheter and that has a working length with a circumferential, ablative band disposed between two insulated and non-ablative end portions.

One circumferential ablation element design that is believed to provide a highly useful embodiment of the present invention is shown in FIG. 2. As described in further detail below, this and other circumferential ablation element designs are believed to be particularly useful for tissue ablation along a region where a pulmonary vein extends from a left atrium in the treatment of atrial fibrillation. As shown in FIG. 2, the design includes a circumferential ablation member (200) with two insulators (202,204) that encapsulate the proximal and distal ends, respectively, of the working length L of an expandable member (210). In the particular embodiment shown, the insulators (202,204) are distinct layers of material that cover a balloon skin (212) of balloon or expandable member (210). By providing these spaced insulators, a circumferential band (203) of uninsulated balloon skin is located between the opposite insulators.

The expandable member (210) as shown in FIG. 2 is joined at its proximal end to elongate body (201) that extends proximal to the expandable member (210). More particularly, FIG. 2 shows the expandable member (210) and the elongate body (201) as being integrally formed, with the elongate body (201) extending from the expandable member (210) to the proximal end of the device outside of the patient (not shown). The distal end of the expandable member (210) is mounted to inner member (221) that extends through the elongate body (201) and expandable member (210) to the proximal end of the device. A lumen within the inner member (221) allows passage of a guidewire, as described in further detail below. The lumen defined between the elongate body (201) and the inner member (221) provides a passageway for fluids used in ablation and/or inflation of balloon (210). It will be appreciated that other designs may also be used for the circumferential ablation member. For instance, the expandable member (210) need not be integral with the elongate body (201), and may be separately mounted.

It is further noted that this embodiment is not limited to a particular placement of the ablation element. Rather, a circumferential band may be formed anywhere along the working length of the expandable member and circumscribing the longitudinal axis of the expandable member as previously described.

The balloon construction shown in FIG. 2 forms an RF ablation electrode. An electrode (220) is provided on inner member (221) and is coupled to an ablation actuator shown at radiofrequency ("RF") current source (230) via electrical lead (225), thereby forming an internal current source within balloon (210). RF current source (230) is coupled to both the RF electrode element and also a ground patch (295) that is in skin contact with the patient to complete an RF ablation circuit. A porous membrane such as an expanded fluoropolymer, and more particularly an expanded polytetrafluoroethylene material, comprises the entire balloon skin (212) of expandable member (210). The porous skin (212) may be constructed according to several different methods, such as by forming holes in an otherwise contiguous polymeric material, including mechanically drilling or using laser energy, or the porous skin may simply be an inherently permeable material with inherent void volume forming pores for permeability, as will be developed according to more particular illustrative embodiments below. By insulating the proximal and distal end portions of the working length of the expandable member as shown in FIG. 2, only the pores along the circumferential band of the uninsulated intermediate region are allowed to ablatively couple the electrolyte which carries an ablative RF current into tissue. This uninsulated intermediate region thus forms a permeable section, while the insulated regions of the expandable member are non-permeable sections.

It will further be appreciated that in the illustrated embodiment where the balloon (210) is integral with the elongate body (201), the elongate body (201) is nonporous to prevent fluid from passing through the wall of the elongate body (201) before reaching the balloon chamber. In another embodiment, the insulator (202) may extend over the elongate body (201) to insulate the elongate body (201). Further details regarding methods and apparatus for making a device permeable in certain portions and non-permeable in other portions are described below.

According to operation of the FIG. 2 assembly, an ablative fluid medium that is electrically conductive, such as for example a hypertonic saline solution, passes from a source (240) and into the internal chamber defined by the skin and outwardly into the porous wall of the balloon skin along the intermediate region until the solution directly couples to tissue. By electrically coupling the fluid within the porous balloon skin to an RF current source (230) via electrode (220), the porous region of the expandable member functions as an RF electrode wherein RF current flows outwardly into the tissue engaged by the balloon via the conductive fluid absorbed into the porous intermediate region of the wall.

The ablation actuator mechanism for the overall assembly, such as including current source (230), may also include or be coupled to a monitoring circuit (not shown) and/or a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

In addition, one further illustrative embodiment (not shown) which is also contemplated provides an outer skin with the selectively porous intermediate region externally of another, separate expandable member, such as a separate expandable balloon, wherein the conductive fluid coupled to a current source is contained in a region between the outer skin and the expandable member contained therein.

FIG. 2 broadly illustrates an ablation balloon construction wherein an ablative surface is provided along the entire working length of an expandable member, but the surface is shielded or insulated from releasing ablative energy into surrounding tissues except for along an unshielded or uninsulated equatorial band. As such, the insulator embodiment contemplates other ablation elements which are provided along the entire working length of an expandable member and which are insulated at their ends to selectively ablate tissue only about an uninsulated equatorial band. Other RF electrode arrangements are also considered suitable for use according to the selectively insulated ablation balloon embodiment shown in FIG. 2. In one further illustrative example, a metallized balloon includes a conductive balloon skin wherein the electrical insulators, such as polymeric coatings, are positioned over or under each end of the working length and thereby selectively ablate tissue with electricity flowing through the uninsulated equatorial band. The balloon skin may itself be metallized, such as by mixing conductive metal, including but not limited to gold, platinum, or silver, with a polymer to form a compounded, conductive matrix as the balloon skin. Or a discrete electrode element may be secured onto an outer surface of the balloon skin, such as in the embodiment when an expandable balloon is placed within an outer skin of selected porosity as just described above. In another example, the porous aspects of the circumferential band are beneficially applied in a chemical ablation element mode, wherein a chemically ablative fluid medium such as an alcohol based medium is absorbed within the wall of the circumferential band and coupled to the tissue engaged to the band for ablation.

In the alternative, or in addition to the RF electrode variations just described, the circumferential ablation member provided by the ablation balloon described may also include other ablative energy sources or sinks, and particularly may include a thermal conductor that circumscribes the outer circumference of the working length of an expandable member. Examples of suitable thermal conductor arrangements include a metallic element that may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40 deg and 80 deg Celsius.

The various alternative ablation elements such as those just described may further incorporate the various other embodiments such as methods of manufacture or use described below, and fall within the present invention.

It is further contemplated that the insulators described may be only partial and still provide the relatively isolated ablative tissue coupling along the circumferential band. For instance, in the conductive RF electrode balloon case, a partial electrical insulator will allow a substantial component of current to flow through the uninsulated portion due to a "shorting" response to the lower resistance in that region. In another illustrative construction, balloon skin (212) may be thermally conductive to surrounding tissue when inflated with a heated fluid which may contain a radiopaque agent, saline fluid, ringers lactate, combinations thereof, or other known fluids having acceptable heat transfer properties for these purposes.

FIG. 2 further shows use of an electrode element (220) as a radiopaque marker to identify the location of the equatorial band (203) in order to facilitate placement of that band at a selected ablation region of a pulmonary vein via X-ray visualization. Electrode element (220) is opaque under X-ray, and may be constructed, for example, of a radiopaque metal such as gold, platinum, or tungsten, or may comprise a radiopaque polymer such as a metal loaded polymer. FIG. 2 shows electrode element (220) positioned coaxially over an inner tubular member (221) which is included in a coaxial catheter design as would be apparent to one of ordinary skill. The present invention contemplates the combination of such a radiopaque marker additionally in the other embodiments herein shown and described. To note, when the circumferential ablation member that forms an equatorial band includes a metallic electrode element, such electrode may itself be radiopaque and may not require use of a separate marker. Moreover, various contemplated designs do not require positioning of the electrode (220) exactly along the band region, and therefore such electrode may be replaced with a simple radiopaque marker in order to retain the ability to locate the band within the body via X-ray visualization.

The expandable member of the embodiments shown may take one of several different forms, although the expandable member is generally herein shown as an inflatable balloon that is coupled to an expansion actuator which is a pressurizeable fluid source. The expandable member forms a fluid chamber which communicates with a fluid passageway (not shown in all the figures) that extends proximally along the elongate catheter body and terminates proximally in a proximal fluid port that is adapted to couple to the pressurizeable fluid source.

The embodiment of FIG. 2 describes the expandable member (210) as being a balloon made of a porous fluoropolymer, such as an expanded polytetrafluoroethylene material. It will be appreciated that various other materials may also be suitable for the balloon, or portions of the balloon, as described for the various embodiments herein.

Several possible balloon materials are described below. These materials may have inherent porosity as would be known to one of skill in the art, or may be made porous according to several different methods, such as forming holes in an otherwise contiguous polymeric material.

In one expandable balloon variation, the balloon or portion thereof may be constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may choose a particular device to meet a particular patient's pulmonary vein anatomy.

In an alternative expandable balloon variation, the balloon may be constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

According to one elastomeric construction that is believed to be highly beneficial for engaging large pulmonary vein ostia, such as ranging from 1–2.5 centimeters in diameter, the balloon is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in diameter that is attributable to the material compliance in a stress-strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion ratio).

Moreover, a circumferential ablation member is adapted to conform to the geometry of the pulmonary vein ostium, at least in part by providing substantial compliance to the expandable member, as will be further developed below. Further to this conformability, such as is shown by reference to FIG. 14A, the working length L of expandable member (1470) is also shown to include a taper which has a distally reducing outer diameter from a proximal end (1471) to a distal end (1473). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Other expandable members than a balloon may also be suitable according to the insulator aspects of the invention. For example, various modes of known expandable cages may be sufficient expandable members for this invention so long as a fluid chamber is at least in part enclosed by or otherwise associated with the cage so as to provide for ablative fluid coupling to tissue as broadly contemplated by the disclosed embodiments.

It is to be appreciated that the circumferential band (203) shown in FIG. 2 and elsewhere throughout the figures generally has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

Further to the relatively narrow circumferential band aspect of the invention, the circumferential lesion formed may also be relatively narrow when compared to its own circumference, and may be less than two-thirds or even one-half its own circumference on the expandable element when expanded. In one arrangement which is believed to be suitable for ablating circumferential lesions in heart chambers or pulmonary veins, the band width w is less than 1 cm with a circumference on the working length when expanded that is greater than 1.5 cm.

Still further to the FIG. 2 embodiment, energy is coupled to the tissue largely via the ablative medium supplied by the inflation fluid and porous or permeable balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, several different balloon types may be provided for ablating different tissue structures so that a particular shape may be chosen for a particular region of tissue to be ablated, such as for example in order to accommodate differing geometries encountered when ablating circumferential regions of tissue to isolate various different pulmonary veins in either the same of different patients, as further developed elsewhere hereunder, and by reference to FIGS. 17–21 below.

The elongate body (201) of the overall catheter assembly shown in FIG. 2, and as appropriate elsewhere throughout this disclosure, may have an outer diameter provided within the range of from about 5 French to about 10 French, and more preferable from about 7 French to about 9 French. In "guidewire tracking designs" as shown in FIG. 2, the guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although the diameter may vary based upon the viscosity of inflation medium used, length of the lumen, and other dynamic factors relating to fluid flow and pressure.

The elongate body (201) should also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion of the body (201) is preferably flexible and adapted to track over and along a guidewire seated within the targeted pulmonary vein. In one further more detailed construction which is believed to be suitable, the proximal end portion is adapted to be at least 30% stiffer than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the circumferential ablation member to the desired ablation region are also contemplated. For example, while the FIG. 2 variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation.

Further to this latter variation, the guidewire lumen and guidewire of the FIG. 2 variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

Figure 3A:
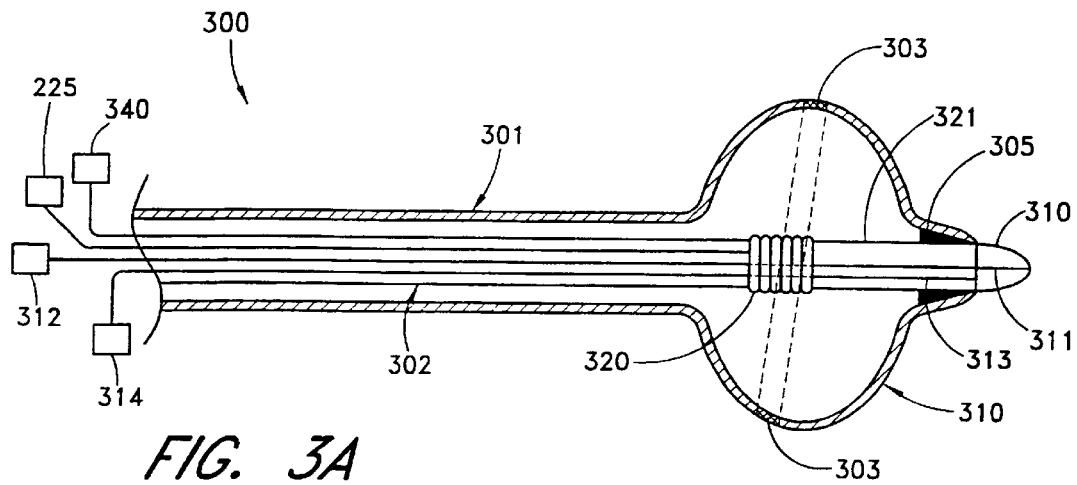
FIGS. 3A–B show longitudinal cross-sectional and perspective views, respectively, of another circumferential ablation device having a similar balloon ablation member as shown in FIG. 2, except showing the balloon ablation member secured to the distal end portion of a steerable delivery member.
Figure 3B:
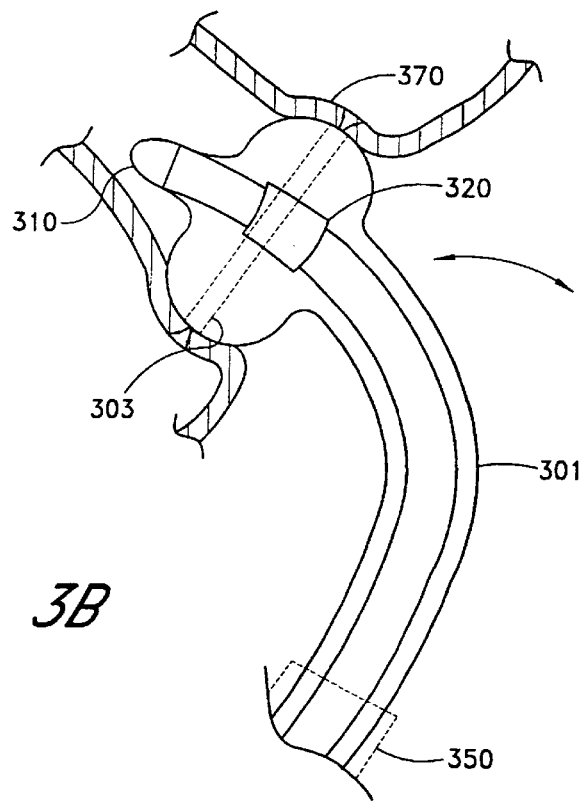

FIGS. 3A–B illustrate such an additional variation of the tissue ablation device assembly (300) wherein an ablation balloon (310) is beneficially secured over a steerable delivery member (302) which may be similar for example to deflectable tip electrode catheter and/or according to various steerable cardiac electrophysiology mapping catheters, such as those known in the art. Outer member (301) is shown coaxially disposed over steerable delivery member (302) such that permeable band (303) of balloon (310) provided by outer sheath (301) is disposed around electrode (320) provided on the steerable delivery member (302). Inflation device (340) is fluidly coupled with the inner fluid chamber formed by balloon (310) and includes a pressurized source of an ablative medium such as electrically conductive fluid. An ablation actuator, which in the 10 FIG. 3A embodiment is RF current source (330), is coupled with electrode (320). Furthermore, tip electrode mapping/actuator assembly (314) is also shown coupled with tip electrode (310) via tip electrode lead (313). Further to the particular variation shown in FIGS. 3A–B, the distal end of pullwire (311) is schematically shown to be secured to the distal end of the steerable delivery member (301), whereas the proximal end of pullwire (311) is shown coupled to deflection actuator (314) which is adapted to controllably provide forces on pullwire (311) such that the distal end of assembly (300) is deflected or shaped as desired for torsional steering.

Balloon (310) is secured to the outer surface (321) of steerable delivery member (302) via bond (305) such that a fluid tight seal is provided and further such that balloon (310) and steerable delivery member (302) are in a fixed relationship to each other such that they may be manipulated and controllably positioned together via transcatheter techniques. In a preferred mode for use shown in FIG. 3B, assembly (300) is shown delivered into a left atrium through a transeptal sheath (350), wherein it is shaped (illustrated by double headed arrows in FIG. 3B) and positioned within a pulmonary vein. More specifically, band (303) is engaged to circumferential region of tissue (370) in order to ablatively couple electrode (320) through band (303) and to tissue (370) via the ablative fluid medium absorbed into the wall of band (303).

The electrode (320) need not be positioned exactly along band (303) relative to the long axis of device assembly (300) in order to electrically couple the electrode to fluid and thereby to the band and tissue surrounding the band. However, as electrode (320) is preferably a radiopaque material such as a metal, and considering an increase in impedance when moving electrode (320) further away from band (303), the embodiment shown is believed to be highly beneficial. If another electrical source were provided such that there were no electrode (320) within balloon (310), then a separate radiopaque band may be provided at a similar location where electrode (320) is shown in FIG. 3A in order to provide a marker to position band (303) where desired, such as along circumferential region of tissue (370) as shown in FIG. 3B.

Figure 4A:
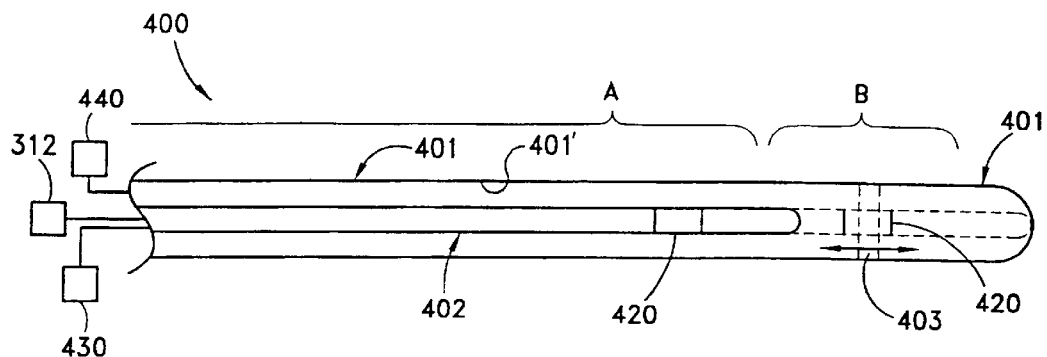
FIGS. 4A–C show various views of a circumferential ablation device similar to that shown in FIGS. 3A–B, except showing the balloon ablation member disposed around a steerable delivery member such that the steerable delivery member is moveable within the balloon ablation member.
Figure 4B:
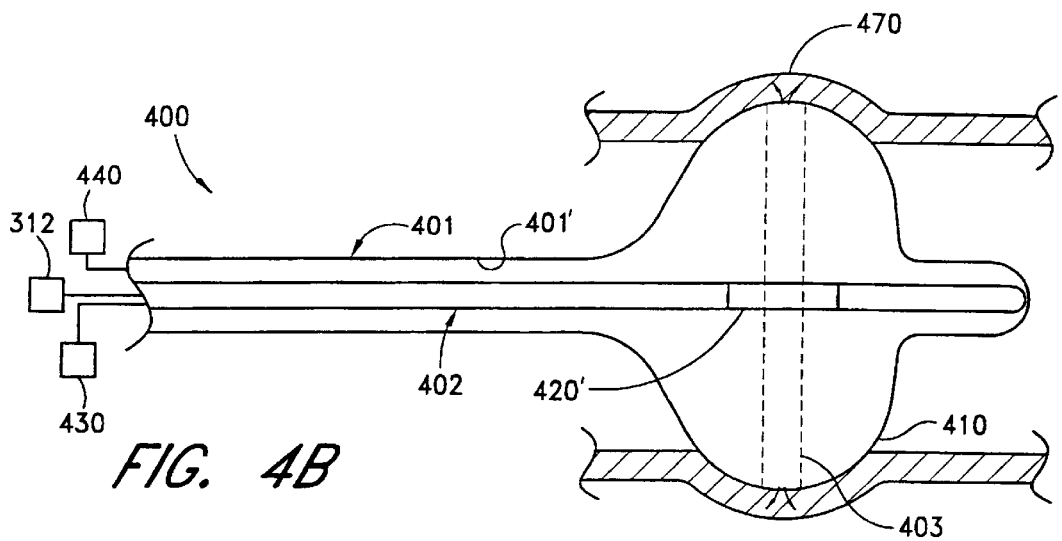
Figure 4C:
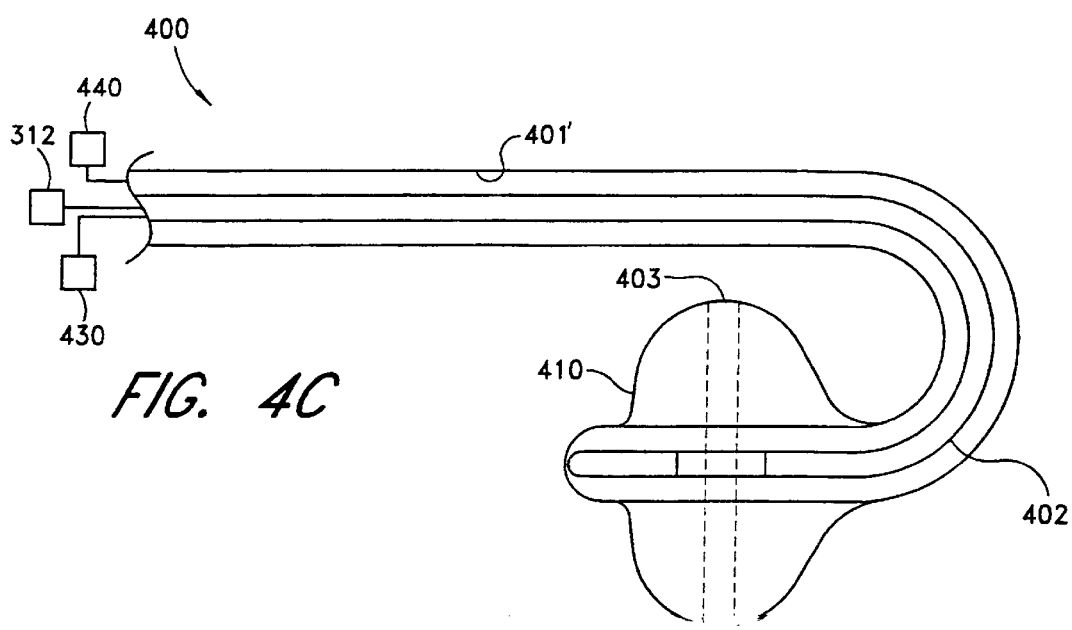

The FIGS. 4A–C embodiment provides a steerable electrode catheter/balloon assembly (400) that differs from the FIGS. 3A–C embodiment in that the steerable delivery member (402) in FIGS. 4A–C is moveably engaged within an interior passageway of a separate outer member (401) that provides balloon (410) in a separate sheath assembly that surrounds steerable delivery member (402). Section A in FIG. 4A indicates the portion of the outer member (401) that does not expand when filled with fluid, while Section B in FIG. 4B defines the balloon portion that does expand when filled with fluid. More specifically, outer member (401) is characterized as being: (a) closed at the distal end; and (b) inflatable along balloon (410) if pressurized with fluid from pressurizeable fluid source (440) containing electrically conductive fluid. By advancing the steerable delivery member (402) within passageway (401'), electrode (420) is aligned with band (403) such that expansion of balloon (410) and actuation of electrode (420) ablates a circumferential band of tissue (470) engaged to band (403), as shown in FIG. 4B. Moreover, as in FIGS. 3A–C, the steerable delivery member (402) is preferably of the deflectable variety known in the art, and therefore allows for controllable positioning of the balloon (410) before, during, or after expansion and circumferential ablation, wherein such deflection is shown for the purpose of illustration in FIG. 4C. Beneficially, however, this FIGS. 4A–C embodiment allows for the outer member (401) to be selectively fit over and used with any commercially available steerable catheters, such as for example commercially available, "deflectable tip" RF ablation catheters.

In order to add the proper positioning of the electrode (420) within the balloon (410) relative to band (403), some form of indicia may be provided on either or both of outer and inner catheters of this assembly, such as either visible markings on portions of the associated members extending externally of the body, or radiopaque markers that allow x-ray guided alignment of the assemblies.

Figure 5A:
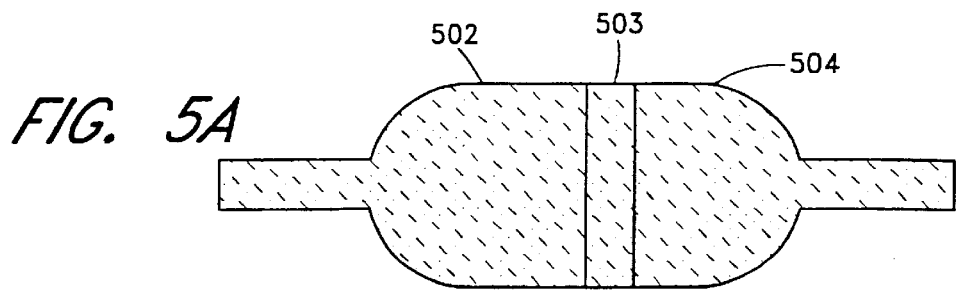
FIGS. 5A–E variously show various modes of one method for manufacturing a balloon for use as a balloon ablation member according to the invention.
Figure 5B:
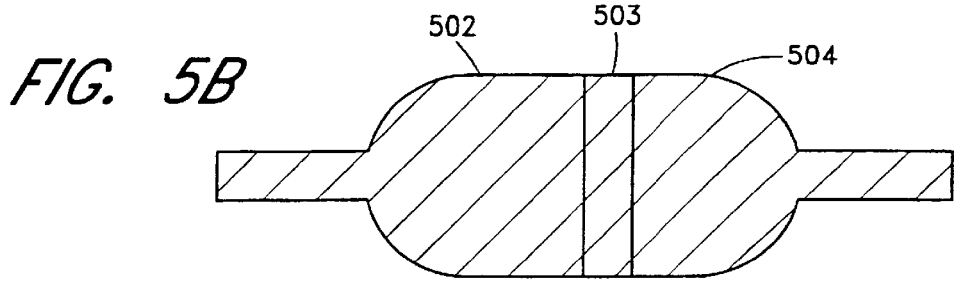
Figure 5C:
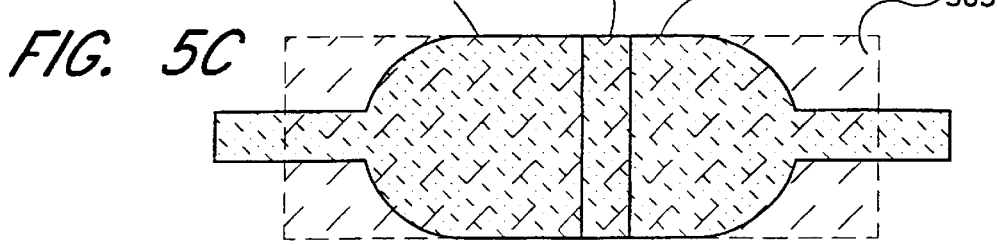

FIGS. 5A–E show various modes for making a porous band along a working length of a circumferential ablation balloon. More specifically, FIGS. 5A–5E show methods for post-processing a pre-formed balloon that is either totally porous (FIG. 5A) or totally non-porous (FIG. 5B), respectively, prior to post-processing. More specifically, FIG. 5C shows a method wherein the totally porous balloon of FIG. 5A is exposed to a filling agent, such as in a dip-coating or other deposition method.

Figure 5D:
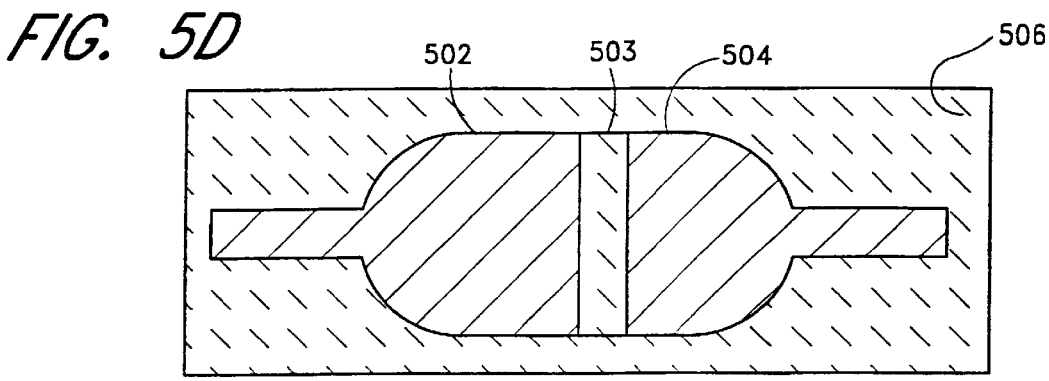
Figure 5E:
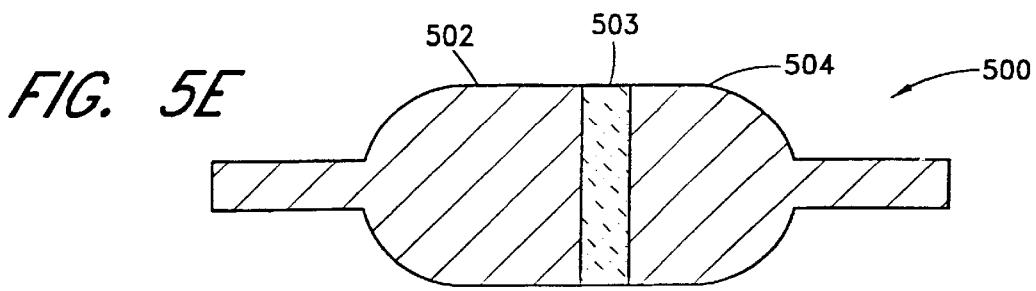

FIG. 5C illustrates the method for treating the totally porous starting balloon of FIG. 5A. Intermediate region (503) is masked off and insulated from being filled during the deposition procedure, and thereafter is left porous when the insulator is removed after filling, leaving only the uninsulated ends non-porous due to the filler (505) introduced into the pores there. In contrast, FIG. 5D illustrates the method using a totally non-porous balloon material from FIG. 5B and masks end portions (502) and (504) while intermediate region or band (503) is left uninsulated and exposed. The bath shown in shadow in FIG. 5D contains not filler for filling the pores along the balloon as was just illustrated for FIG. 5C, but instead contains a solvent (506) that removes material where exposed to the balloon, for example from filled pores to be cleansed and opened for fluid flow.

The method just described for selectively masking the intermediate region and then exposing the entire balloon to filler may be modified. Without masking the porous balloon, the two end portions of the balloon may be dipped into a filler, such that the intermediate region is "undipped" or left out of the dipping material and the only region left porous according to the invention.

Figure 6A:
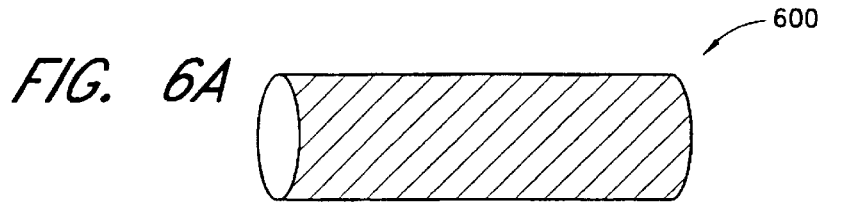
FIGS. 6A–D variously show various modes of another method for manufacturing a balloon for use as a balloon ablation member according to the invention.
Figure 6B:
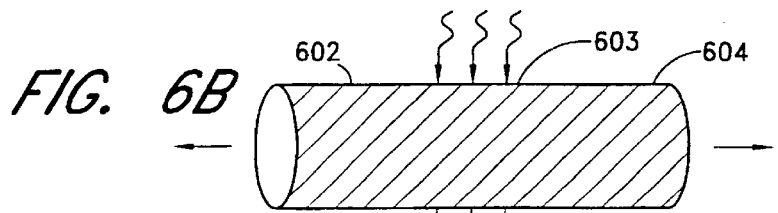
Figure 6C:
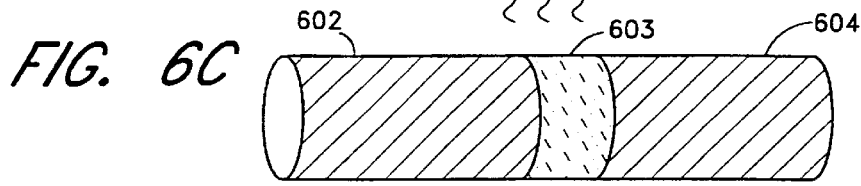
Figure 6D:
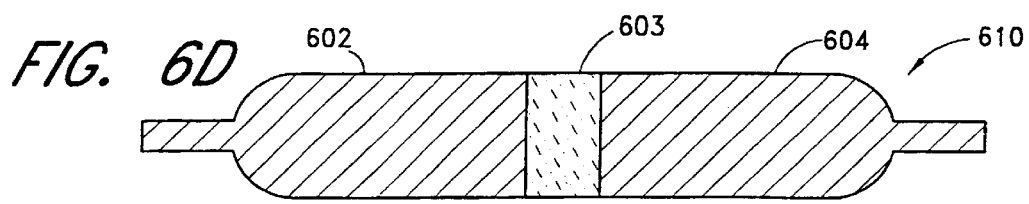
Figure 7A:
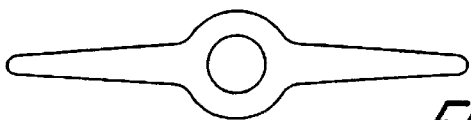
FIGS. 7A–D show schematic axial cross-sectional views of various types of fold patterns for at least a portion of a balloon ablation member in a radially collapsed position according to the invention.
Figure 7B:
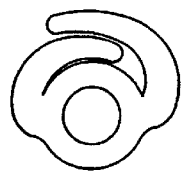
Figure 7C:
Figure 7D:
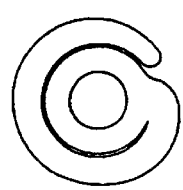

The method illustrated by reference to FIG. 6A allows for the formation of the discrete intermediate permeable band (603) when a base product or tube (600) of a non-expanded, relatively non-permeable fluoropolymer or similar material is used. More specifically, FIG. 6B shows tube (600) being stretched (see illustrative arrows) while only intermediate region (603) is being heated, at the exclusion of end portions (602) and (604) in order to isolate deformation along that intermediate region (603). Such deformation is known to "expand" the substrate fluoropolymer such that the node and fibril network is stretched with larger void volumes than in the relatively "un-expanded" end portions. Accordingly, intermediate region (603) is left as a circumferential, permeable band of expanded fluoropolymer. The end portions of such selectively expanded tube may be incorporated onto a delivery and ablation source assembly such as according to the embodiments elsewhere herein described, such as by forming the tube into a balloon (610) as shown in FIG. 6D and then adapting it to the distal end of an over-the-wire ablation catheter assembly or deflectable tip inner electrode catheter. Since fluoropolymer is generally inelastic, such a balloon may beneficially be folded for in vivo delivery to the left atrium and pulmonary vein. Examples of such folds are variously shown throughout FIGS. 7A–D.

Fluid permeable fluoropolymer such as polytetrafluoroethylene may also be provided only along the intermediate region, wherein the end portions of the working length of the ablation balloon are formed from another material grafted or otherwise secured to the permeable intermediate material, as variously shown by example and without limitation in FIGS. 8A–10E.

Figure 8A:
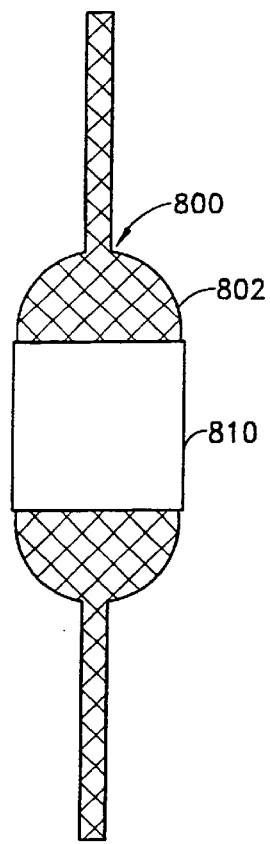
FIGS. 8A–C show perspective views of various modes of another method for manufacturing a balloon for use as a balloon ablation member according to the invention.
Figure 8B:
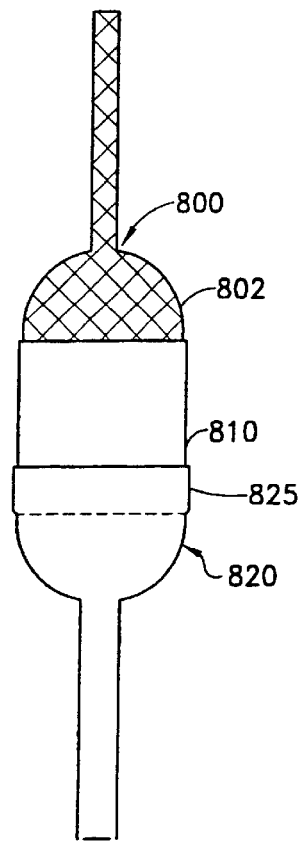
Figure 8C:
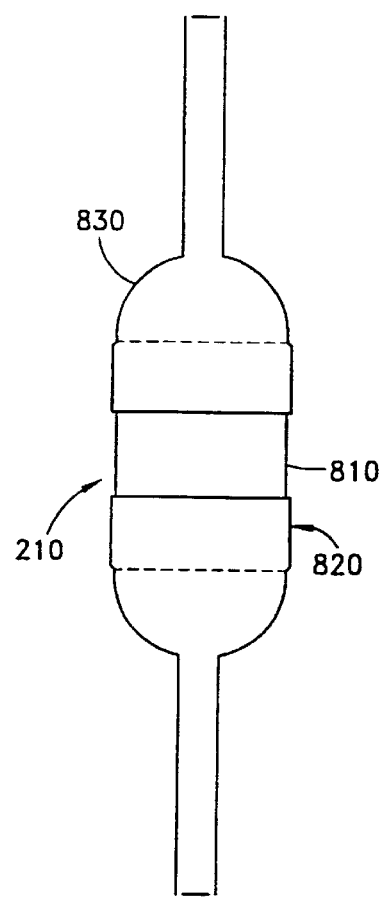

More specifically FIGS. 8A–C show a method for constructing such a balloon with varied material composition over the working length. FIG. 8A shows a mandrel (800) with an enlarged region (802) sized to support permeable tubing (810), which may be for example a fluoropolymer such as an expanded PTFE material. An elastic member (820) is advanced over one narrow end of mandrel (800) until it elastically is forced open as it is advanced over the enlarged region (802) and further over permeable tubing (810) to create an overlap zone (825), as shown in FIG. 8B. The same is done on the opposite side, as shown in FIG. 8C, to produce the final grafted balloon that may be then removed from the mandrel.

Figure 9A:
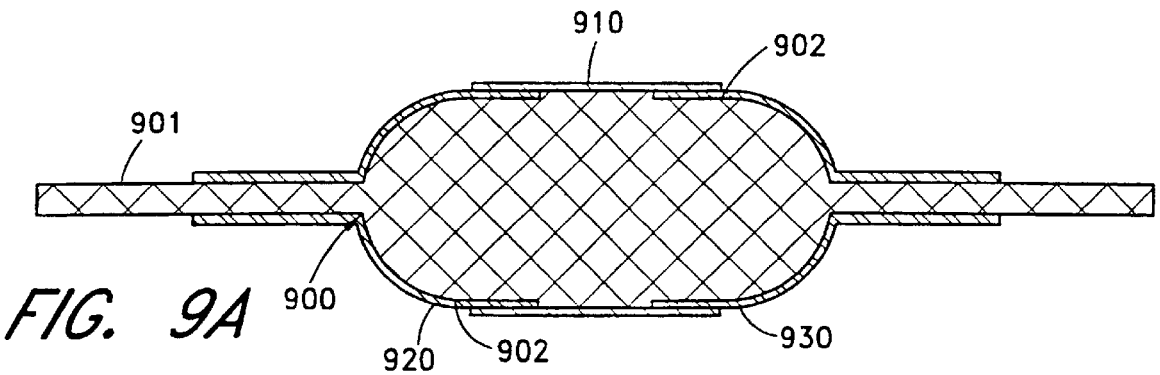
FIGS. 9A–C show longitudinal cross-sectional views, with respect to FIGS. 9A–B, and a perspective overview, with respect to FIG. 9C, illustrating various modes of another method for manufacturing a balloon for use as a balloon ablation member according to the invention.
Figure 9B:
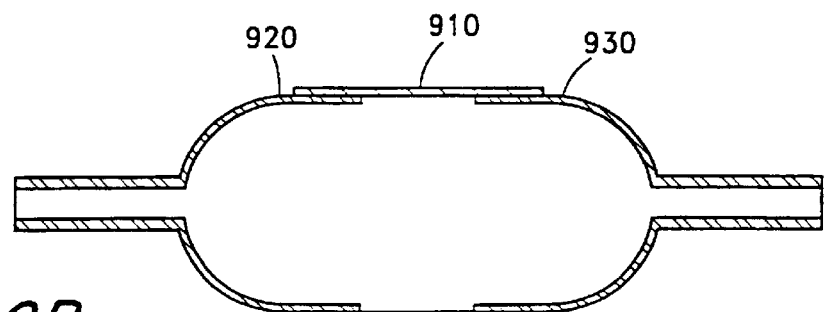
Figure 9C:
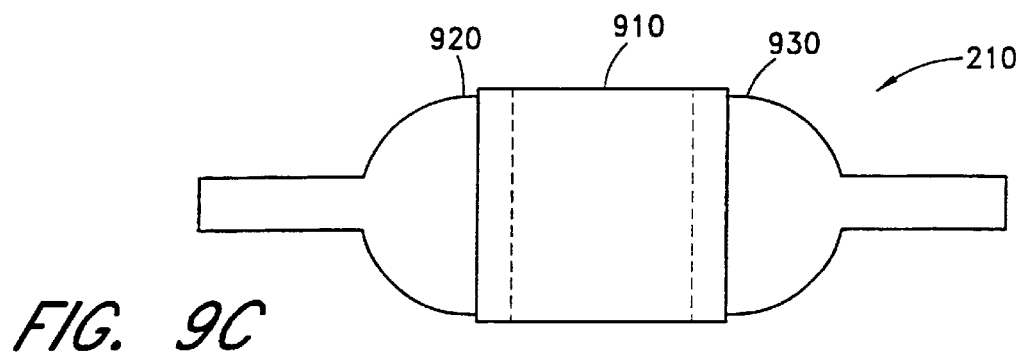

This particular method just described may be varied, such as for example as is shown in FIGS. 9A–B wherein the end portions (920,930) are provided over the mandrel (902) first, and then the PTFE membrane (910) is provided over the end portions to form the requisite overlap zones to result in a contiguous balloon (FIG. 9C).

Figure 10A:
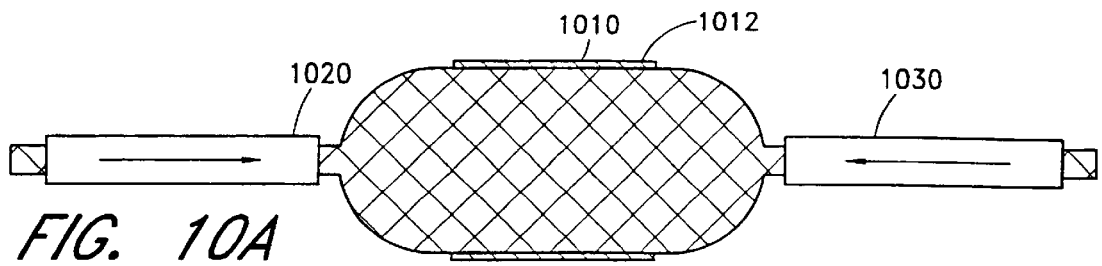
FIGS. 10A–E show various modes of another method for manufacturing a balloon for use as a balloon ablation member according to the invention.
Figure 10B:
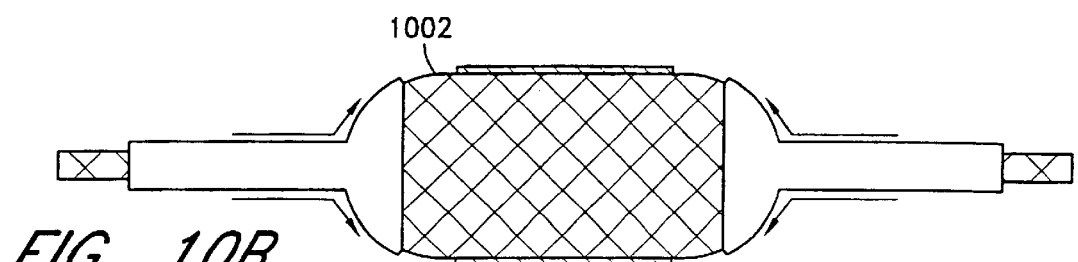
Figure 10C:
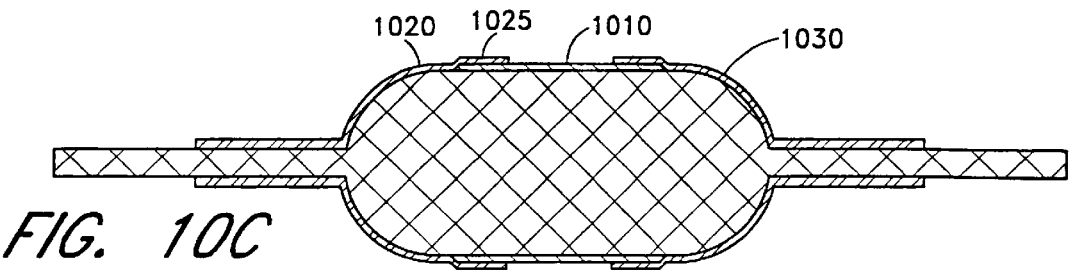
Figure 10D:
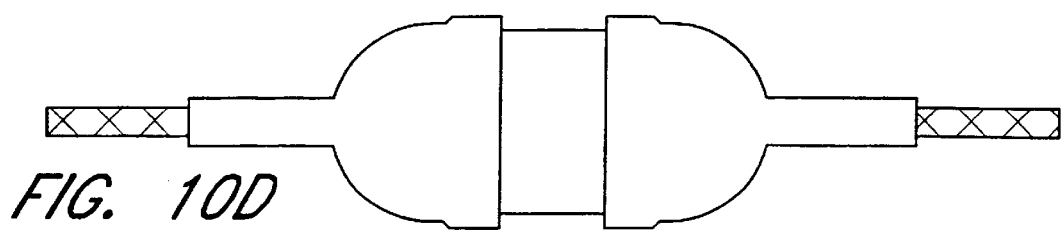
Figure 10E:
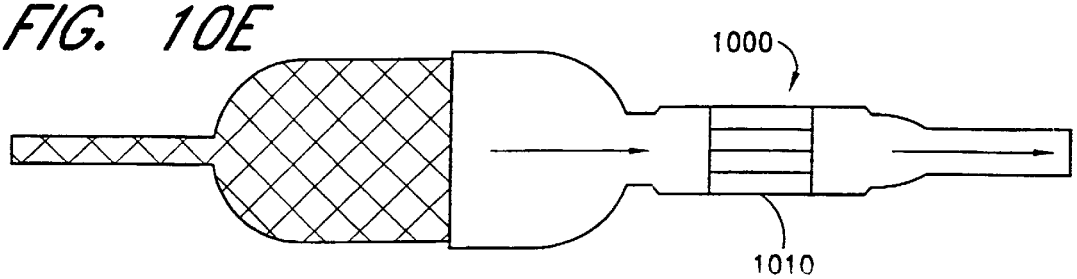
Figure 11A:
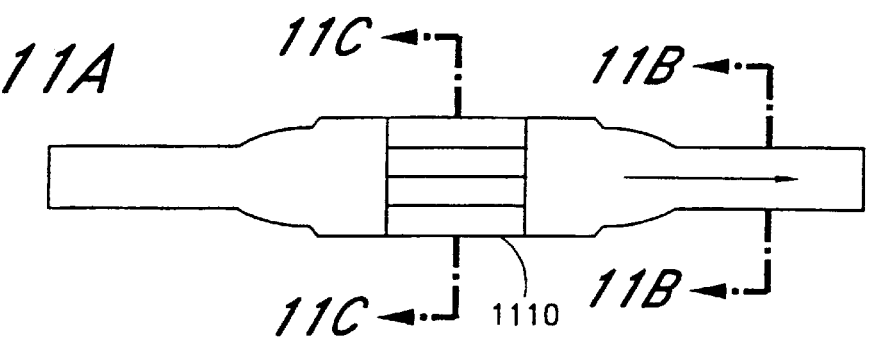
FIGS. 11A–C show a side perspective view and two axial cross-sectional views, respectively, of a final balloon ablation member, wherein a circumferential ablative band provided along the working length of the balloon is shown in a folded configuration when the balloon is in a radially collapsed condition.
Figure 11B:
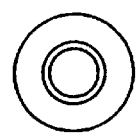
Figure 11C:
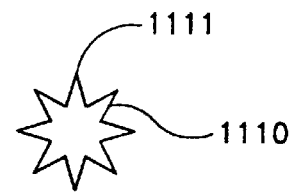
Figure 11D:
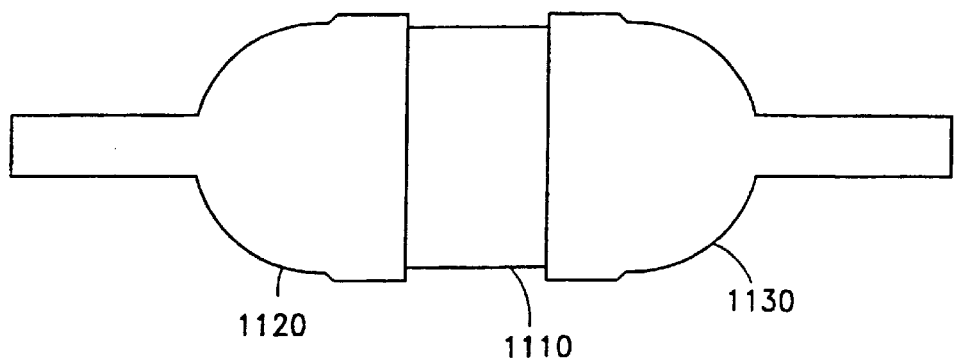
FIG. 11D shows a radially expanded condition for an balloon ablation member such as that shown in FIGS. 11A–C.

According to the methods illustrated in one mode in FIGS. 8A–C and in another mode in FIGS. 9A–C, the elastomeric end portions may be bonded to the permeable membrane along the intermediate region according to a variety of methods. In one variation, the end portions are thermoplastic polymers that may be melted and then flow into the pores of the permeable membrane. However, a separate bonding agent such as a solvent bonding agent or an adhesive may also be used to accomplish the bonding along the overlap region, as is shown by use of bonding agent (1012) by reference to FIGS. 10A–D in a similar method to that shown in FIGS. 8A–C. FIG. 10E shows balloon (1000) being removed from the mandrel after formation according to the method illustrated in FIGS. 10A–D, and further illustrates the novel result of the present method which provides a balloon having elastomeric end portions with a relatively non-elastomeric intermediate region (1010). This relationship is further illustrated in various views of balloon (1000) in FIGS. 11A–D, showing one mode for folding the relatively non-elastomeric intermediate region (1010) while the balloon is in a deflated or radially collapsed condition in FIGS. 11A–C, and another mode for the assembly in the inflated or radially expanded condition in FIG. 11D.

FIGS. 12A–D show various modes of porous fluoropolymer, or more specifically polytetrafluoroethylene (PTFE), which is believed to be a highly beneficial material for use in the assemblies and methods according to the present invention, and in particular the porous circumferential band embodiments. More specifically, expanded PTFE as shown at porous material (1200) generally includes a plurality of nodes (1202) and interconnecting fibrils (1204) which form a network. In the FIG. 12A variation, between these nodes and fibrils are voids (1206) which provide the porosity or permeability desired for a particular application of the ablation assemblies and methods of the present invention. It will be appreciated that any of a number of different pore sizes may be appropriate depending on the particular application. Accordingly, the specific material used for the application may be selected from a variety of commercially available materials having different pore sizes.

Figure 12A:
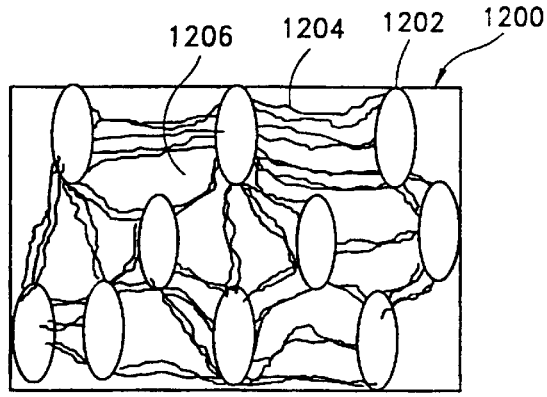
FIG. 12A shows a schematic view of the microscopic structure for one type of expanded fluoropolymer for use in forming a porous circumferential band along a balloon of a circumferential ablation member according to the invention.
Figure 12B:
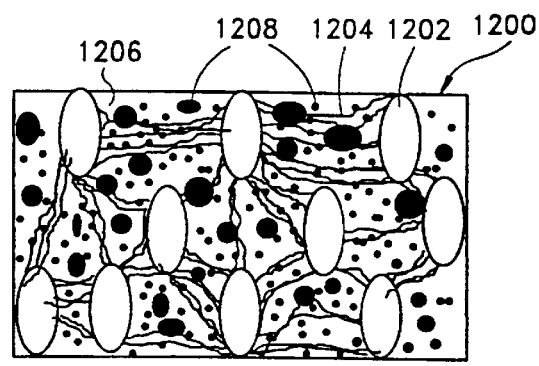
FIG. 12B shows a schematic view of a similar microscopic fluoropolymer structure as that shown in FIG. 12A, except further showing the inclusion of a filler substrate within void or pore regions in the node-fibril network of the expanded fluoropolymer.

As further shown in FIG. 12B, the voids (1206) may also be filled with a filler (1208) such that permeability is attenuated or completely blocked. U.S. Pat. No. 5,753,358 to Korleski, and U.S. Pat. No. 5,766,750 to Korleski, the entirety of both of which are hereby incorporated by reference, disclose an adhesive composite material comprising an expanded fluoropolymer with nodes and interconnected fibrils, the fluoropolymer having a void volume which is at least partially filled by any of a number of fillers. Any of the biocompatible and nontoxic fillers disclosed in these patents may be appropriate for use in accordance with the embodiments of the present invention. Such a construction may be appropriate for the methods of manufacturing an ablation balloon as shown and described above by reference to FIGS. 5A–E. For example, a starting material according to FIG. 12A may be provided for the method illustrated by reference to FIGS. 5A and C, wherein intermediate region (503) is masked while filler (1208) fills all the void volumes along end portions (502,504). The result is a construction along intermediate region (503) that is consistent with FIG. 12A, but a construction along end portions (502,504) that is consistent with FIG. 12B. In contrast, the whole balloon may be filled in a construction consistent with FIG. 12B and then the filler selectively moved from only the intermediate portion (503), yielding a similar result just described.

Figure 12C:
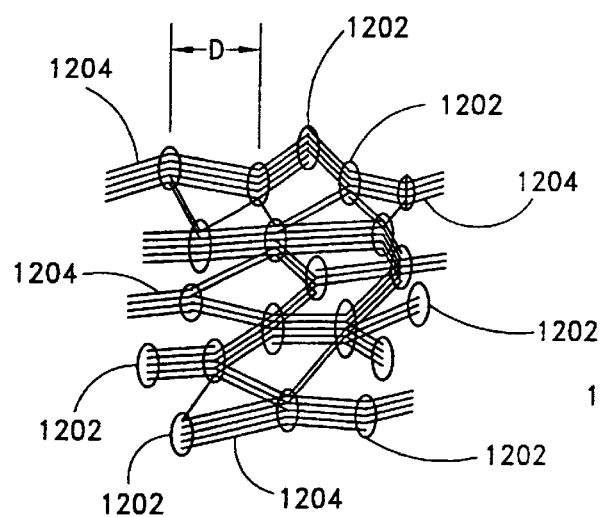
FIGS. 12C–D compare schematic views of the microscopic structures for one type of uniformly expanded polytetrafluoroethylene (PTFE) material and another type of selectively expanded polytetrafluoroethylene (PTFE) material.
Figure 12D:
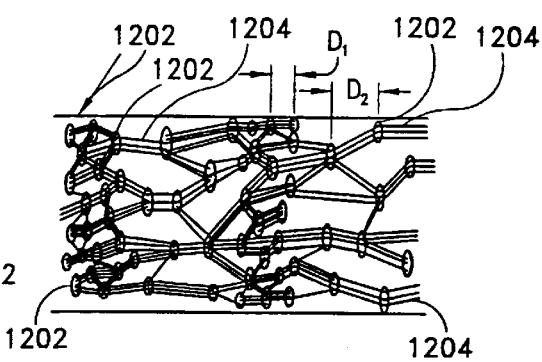

A comparison of FIGS. 12C and D also further illustrates a selective porosity embodiment along a contiguous fluoropolymeric balloon construction (fluoropolymer integral along whole working length of balloon), such as according to the method shown and described by reference to FIGS. 6A–D. More specifically considering the structure shown in FIG. 12D by reference to FIGS. 6A–D, end portions (602, 604) shown in FIGS. 6C or D may have a material construction consistent with for example the denser, less expanded region of compacted nodes (1202) designated by their distance D1 in FIG. 12D. The porous region (603) however would be representative of the more expanded region designated by the inter-nodule distance D2 in FIG. 12D. Thus, by providing varying regions of density and material "expansion" along the balloon working length, the selected intermediate region of permeability for ablation may be achieved.

The embodiments just described are believed to be particularly useful in catheter assemblies which are specifically adapted for ablating tissue along a region where a pulmonary vein extends from a left atrium in the treatment of atrial fibrillation. Therefore, the assemblies and methods of the present invention are also contemplated for use in combination with, or where appropriate in the alternative to, the various particular features and embodiments shown and described in the following U.S. Patents and Patent Applications that also address circumferential ablation at a location where a pulmonary vein extends from an atrium: U.S. Pat. No. 6,024,740 for "CIRCUMFERENTIAL ABLATION DEVICE ASSEMBLY" to Michael D. Lesh et al., filed Jul. 8, 1997; U.S. Pat. No. 6,012,457 for "DEVICE AND METHOD FOR FORMING A CIRCUMFERENTIAL CONDUCTION BLOCK IN A PULMONARY VEIN" to Michael D. Lesh, issued Jan. 11, 2000; U.S. Pat. No. 6,117,101 for "CIRCUMFERENTIAL ABLATION DEVICE ASSEMBLY" to Chris J. Diederich et al., issued Sep. 12, 2000; and U.S. Ser. No. 09/260,316 for "DEVICE AND METHOD FOR CONDUCTION BLOCK IN A PULMONARY VEIN" to Michael D. Lesh. The disclosures of these references are herein incorporated in their entirety by reference thereto. For the purpose of further illustration, FIGS. 13A–15C show sequential modes for using a circumferential ablation catheter assembly in treating atrial fibrillation. Where use according to an "over-the-wire" delivery mode is herein shown and described, it is further contemplated that other delivery modes such as the deflectable steerable modes described above referring to FIGS. 3A–4C.

A patient diagnosed with atrial arrhythmia is treated according to one embodiment of the present invention by forming a circumferential conduction block using the device assemblies herein described. The term "diagnose", including derivatives thereof, is intended to include patients suspected or predicted to have atrial arrhythmia, in addition to those having specific symptoms or mapped electrical conduction indicative of atrial arrhythmia. In one aspect, a patient diagnosed with multiple wavelet arrhythmia originating from multiple regions along the atrial wall may also be treated in part by forming the circumferential conduction block, although as an adjunct to forming long linear regions of conduction block between adjacent pulmonary vein ostia in a less-invasive "maze"-type catheter ablation procedure. In another aspect of the method using the present invention, a patient diagnosed with focal arrhythmia originating from an arrhythmogenic origin or focus in a pulmonary vein is treated according to this method when the circumferential conduction block is formed along a circumferential path of tissue that either includes the arrhythmogenic origin or is between the origin and the left atrium. In the former case, the conduction block destroys the arrhythmogenic tissue at the origin as it is formed through that focus. In the latter case, the arrhythmogenic focus may still conduct abnormally, although such aberrant conduction is prevented from entering and affecting the atrial wall tissue due to the intervening circumferential conduction block.

The sequential steps of a method for using the circumferential ablation device assembly according to one embodiment of the present invention in forming a circumferential conduction block at a location where a pulmonary vein extends from a posterior left atrial wall include: positioning a circumferential ablation element at an ablation region along the location; and thereafter ablating a continuous circumferential region of tissue along the location.

Further to one positioning aspect of the invention, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brockenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using the circumferential ablation device assembly of the present invention. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to gaining transeptal access to the left atrium as just described, a guidewire is then advanced into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as, for example, by using one of the directional catheters disclosed in U.S. Pat. No. 5,575,766 to Swartz, the entirety of which is hereby incorporated by reference. Or, the guidewire may have sufficient stiffness and maneuverability in the left atrial cavity to unitarily subselect the desired pulmonary vein distally of the guiding catheter seated at the fossa ovalis.

Suitable guidewire designs for use in the overall circumferential ablation device assembly of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" may be suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity. Subsequent to gaining pulmonary vein access, the distal end portion of a circumferential ablation device assembly is then tracked over the guidewire and into the pulmonary vein, followed by positioning a circumferential ablation element at an ablation region of the pulmonary vein where the circumferential conduction block is to be desirably formed.

Figure 13A:
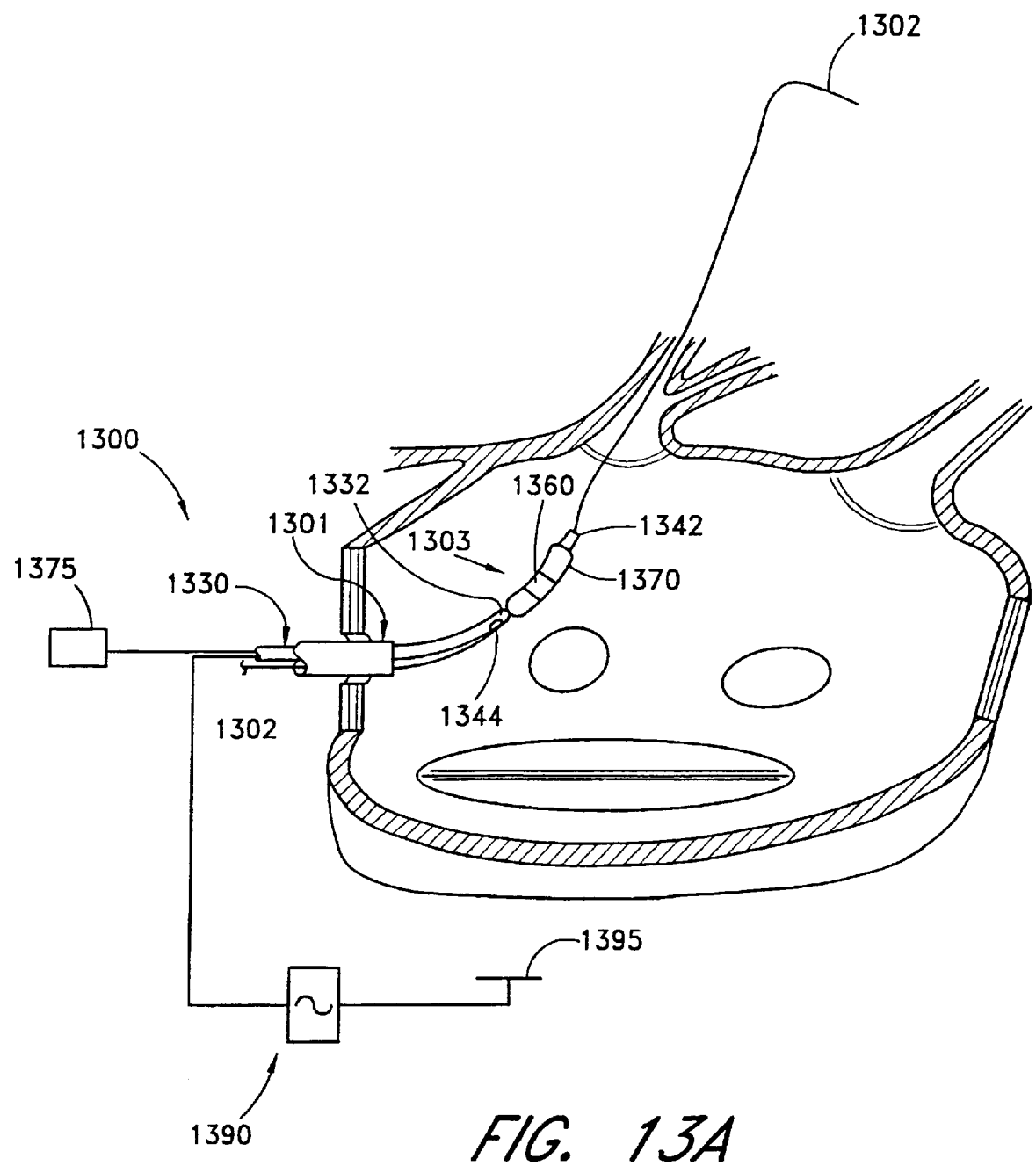
FIGS. 13A–B show various modes of using one type of circumferential ablation device in order to ablate a circumferential region of tissue at a location where a pulmonary vein extends from an atrium according to one mode of the invention.

FIG. 13A shows a circumferential ablation device system (1300) according to one embodiment of the present invention during use as just described, which circumferential ablation system (1300) includes a guiding catheter (1301), guidewire (1302), and circumferential ablation catheter (1303).

More specifically, FIG. 13A shows guiding catheter (1301) subsequent to performing a transeptal access, and also shows guidewire (1302) subsequent to advancement and positioning within a pulmonary vein. FIG. 13A shows circumferential ablation catheter (1303) as it tracks coaxially over guidewire (1302) with a distal guidewire tracking member, which is specifically shown only in part at first and second distal guidewire ports (1342,1344) located on the distal end portion (1332) of an elongate catheter body (1330). A guidewire lumen (not shown) extends between the first and second distal guidewire ports (1342,1344) and is adapted to slideably receive and track over the guidewire. In the particular variation of FIG. 13A, the second distal guidewire port (1342) is located on a distal end portion (1332) of the elongate catheter body (1330), although proximally of first distal guidewire port (1342).

As would be apparent to one of ordinary skill, the distal guidewire tracking member configuration shown in FIG. 13A and just described has the following attributes normally associated with "rapid exchange" or "monorail" catheters according to persons of ordinary skill. For example, such assembly may be easily slideably coupled to the guidewire externally of the body in a "backloading" technique after the guidewire is first positioned in the pulmonary vein and without the need for extra long wires. Furthermore, this guidewire tracking variation removes the need for a guidewire lumen in the proximal portions of the elongate catheter body (1330), which allows for a reduction in the outer diameter of the catheter shaft in that region. Nevertheless, a catheter according to the invention may instead incorporate a design which places the second distal guidewire port on the proximal end portion of the elongate catheter body, as would be normally associated with "over-the-wire" catheters according to one of ordinary skill.

In addition, the inclusion of a guidewire lumen extending within the elongate body between first and second ports, as provided in FIG. 13A, should not limit the scope of acceptable guidewire tracking members according to the present invention. Other guidewire tracking members which form a bore adapted to slideably receive and track over a guidewire are also considered acceptable, such as, for example, the structure adapted to engage a guidewire as described in U.S. Pat. No. 5,505,702 to Arney, the entirety of which is hereby incorporated by reference herein.

While the assemblies and methods shown variously throughout the Figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

Figure 13B:
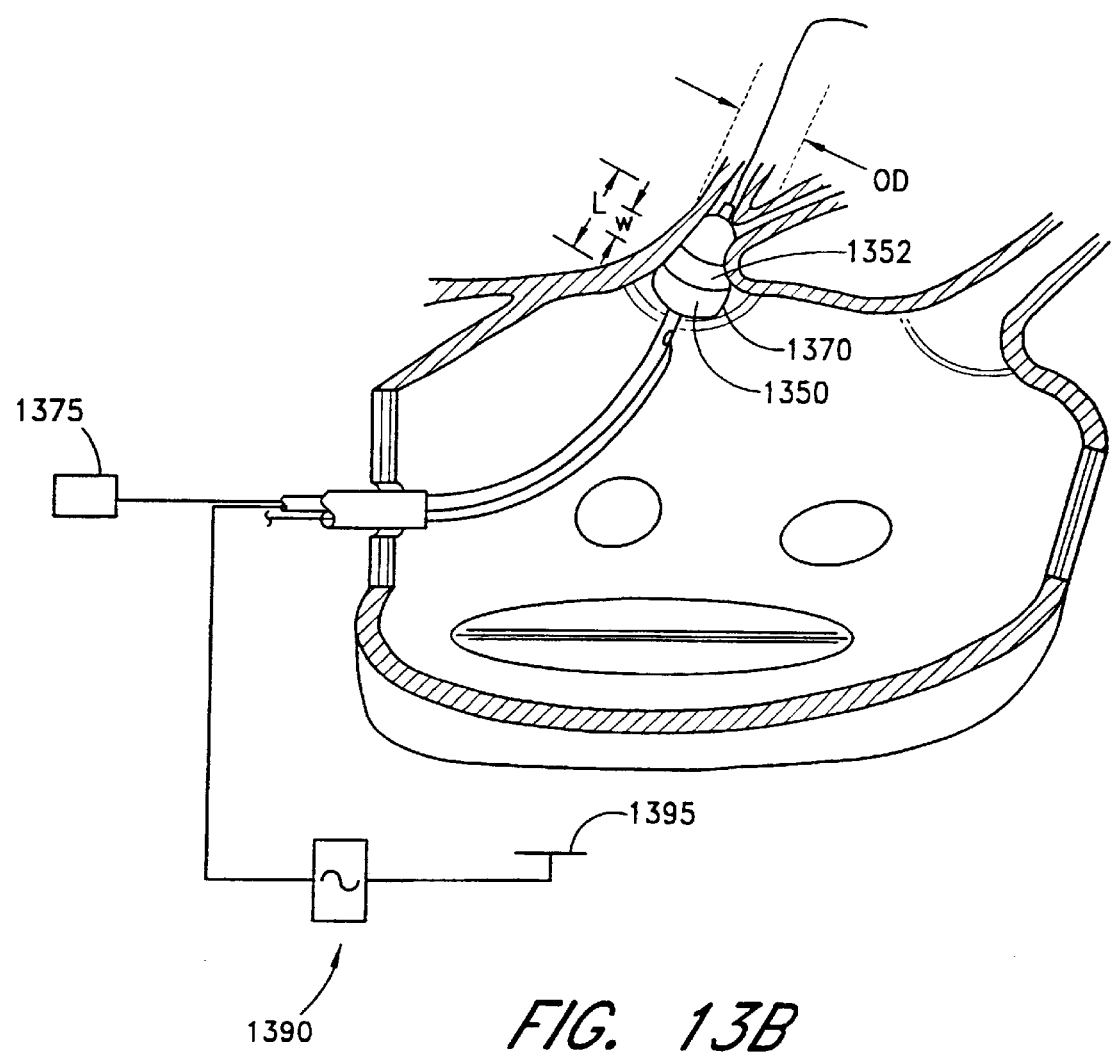

FIG. 13A also shows circumferential ablation catheter (1303) with a circumferential ablation element (1360) formed on an expandable member (1370). The expandable member (1370) is shown in FIG. 13A in a radially collapsed position adapted for percutaneous translumenal delivery into the pulmonary vein. However, expandable member (1370) is also adjustable to a radially expanded position when actuated by an expansion actuator (1375), as shown in FIG. 13B. Expansion actuator (1375) may include, but is not limited to, a pressurizeable fluid source. According to the expanded state shown in FIG. 13B, expandable member (1370) includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation element (1360) also includes a circumferential band (1352) on the outer surface of working length L which is coupled to an ablation actuator (1390) at a proximal end portion of the elongate catheter body (shown schematically). After expandable member (1370) is adjusted to the radially expanded position and at least a portion of working length L circumferentially engages the pulmonary vein wall in the ablation region, the circumferential band (1352) of the circumferential ablation element (1360) is actuated by ablation actuator (1390) to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

More specific to the porous balloon electrode embodiments of the invention, RF energy is delivered to the circumferential region of tissue in part by delivering RF energy from the ablation actuator to electrodes via electrical leads. At the same time, electrically conductive fluid, such as saline, is directed into the fluid chamber formed by balloon and is absorbed into the void volume of permeable circumferential band, whereby electrical current may flow from the electrode, through the fluid, across the wall of balloon, and into the circumferential region of tissue.

A perfusion lumen may be formed within the distal end portion (1332) of elongate catheter body (1330). The perfusion lumen may for example be formed between a distal perfusion port, such as at distal guidewire port (1342), and a proximal perfusion port (1344) which may be formed through the wall of the elongate catheter body (1330) and communicate with the guidewire lumen (not shown) which also forms the perfusion lumen between the distal and proximal perfusion ports. In the particular design shown, after the guidewire has provided for the placement of the ablation element into the pulmonary vein, the guidewire is withdrawn proximally of the proximal perfusion port (1344) (shown schematically in shadow) so that the lumen between the ports is clear for antegrade blood flow into the distal perfusion port (1342), proximally along the perfusion lumen, out the proximal perfusion port (1344) and into the atrium (perfusion flow shown schematically with arrows).

Figure 13C:
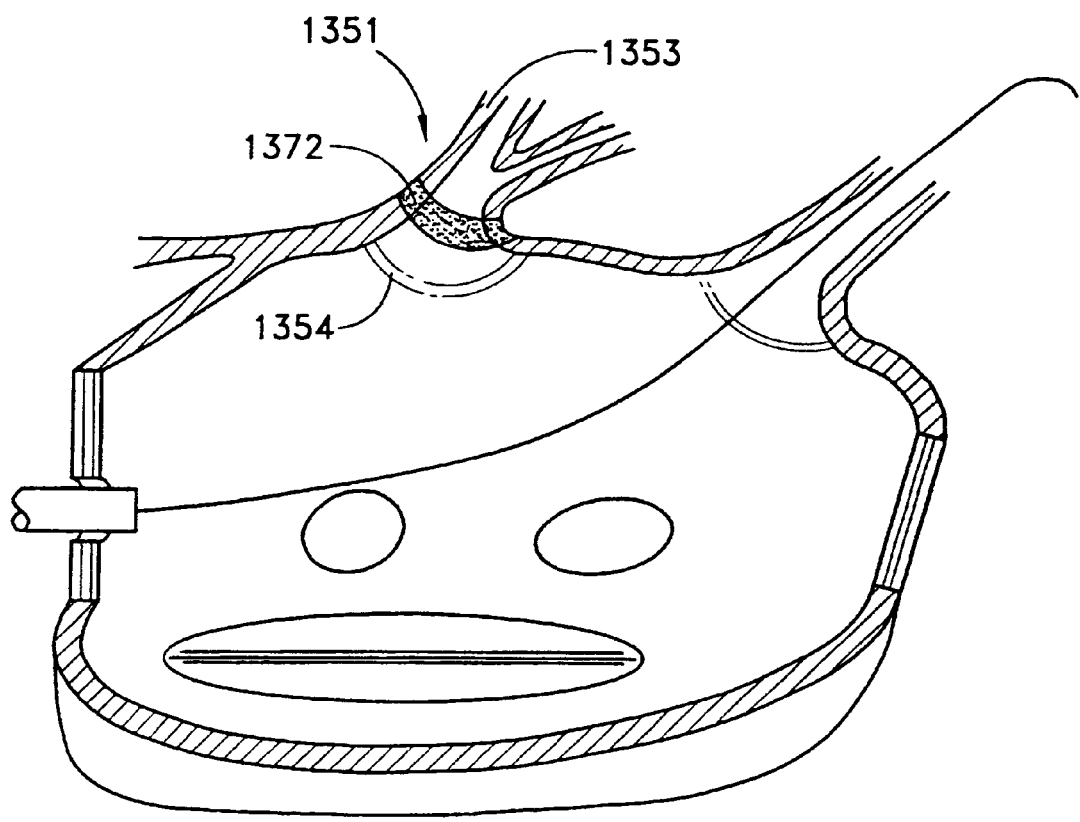
FIG. 13C shows a sectional view of a circumferential conduction block in a pulmonary vein as formed by a circumferential ablation device such as according to the modes shown in FIGS. 13A–B.

FIG. 13C shows the pulmonary vein (1351) after removing the circumferential ablation device assembly subsequent to forming a circumferential lesion (1372) around the ablation region of the pulmonary vein wall (1353) according to the use of the circumferential ablation device assembly shown in stepwise fashion in FIGS. 13A–B. Circumferential lesion (1370) is shown located along the pulmonary vein adjacent to the pulmonary vein ostium (1354), and is shown to also be "transmural," which is herein intended to mean extending completely through the wall, from one side to the other. Also, the circumferential lesion (1370) is shown in FIG. 13C to form a "continuous" circumferential band, which is herein intended to mean without gaps around the pulmonary vein wall circumference, thereby circumscribing the pulmonary vein lumen. Various other references to similar anatomical locations or structures are elsewhere made throughout this disclosure with similar reference numerals attached to the end of the respective figure number (e.g., expandable member 1370 in FIG. 13A is referred to as expandable member 1470 in FIG. 14A).

It is believed, however, that circumferential catheter ablation with a circumferential ablation element according to the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 14A:
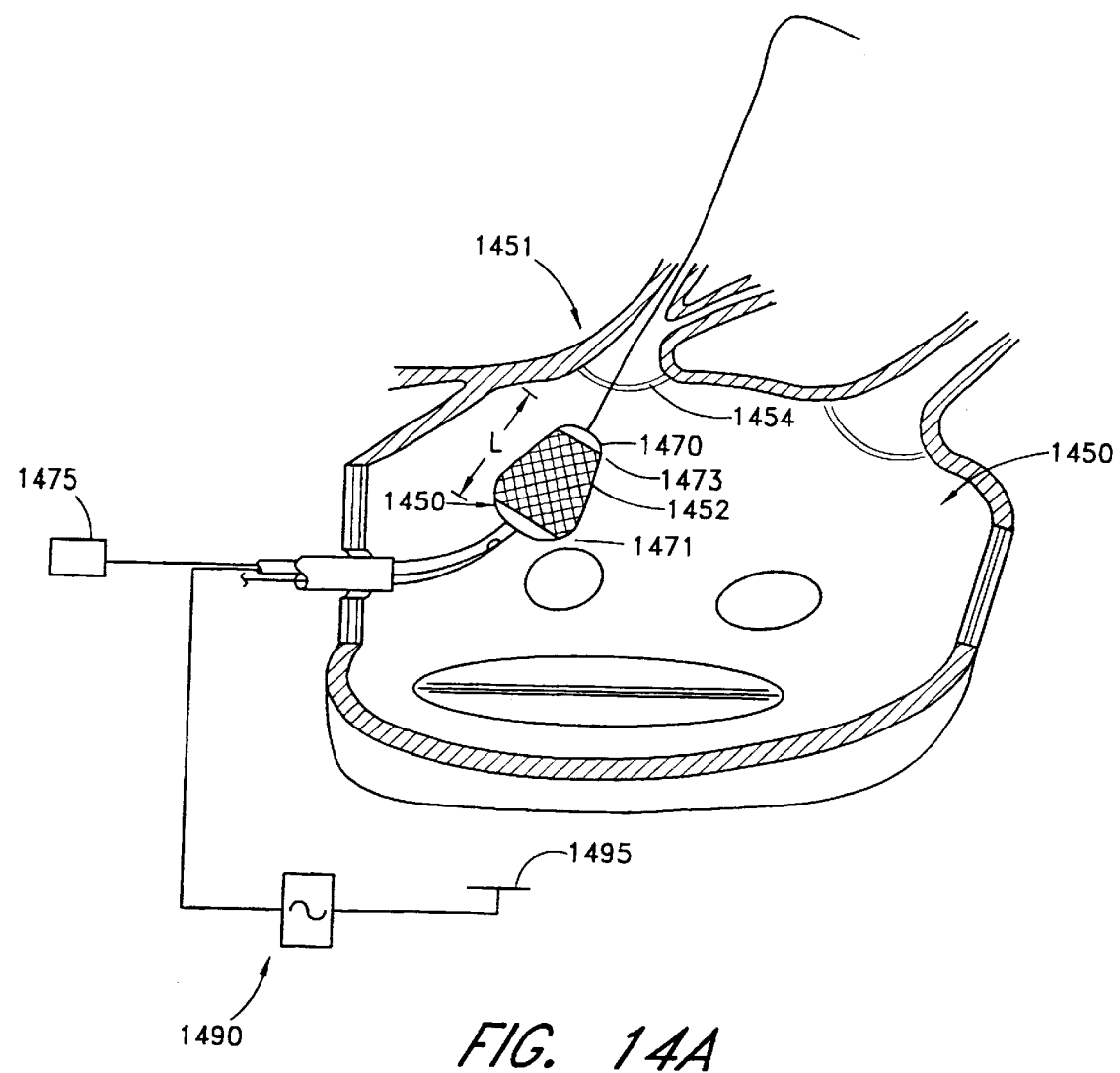
FIGS. 14A–B show various modes of using a circumferential ablation device to ablate a circumferential region of tissue along a location where a pulmonary vein extends from an atrium according to another mode of the invention.
Figure 14B:
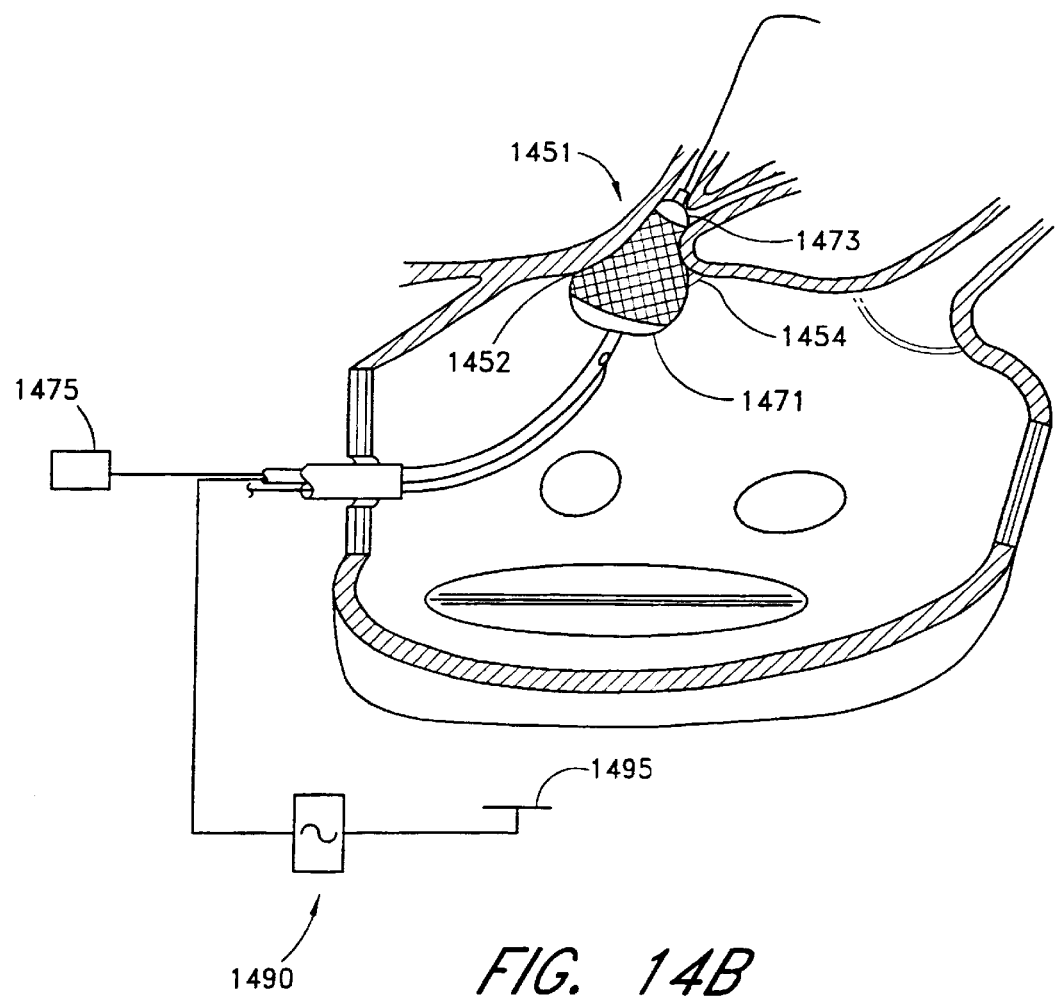
Figure 14C:
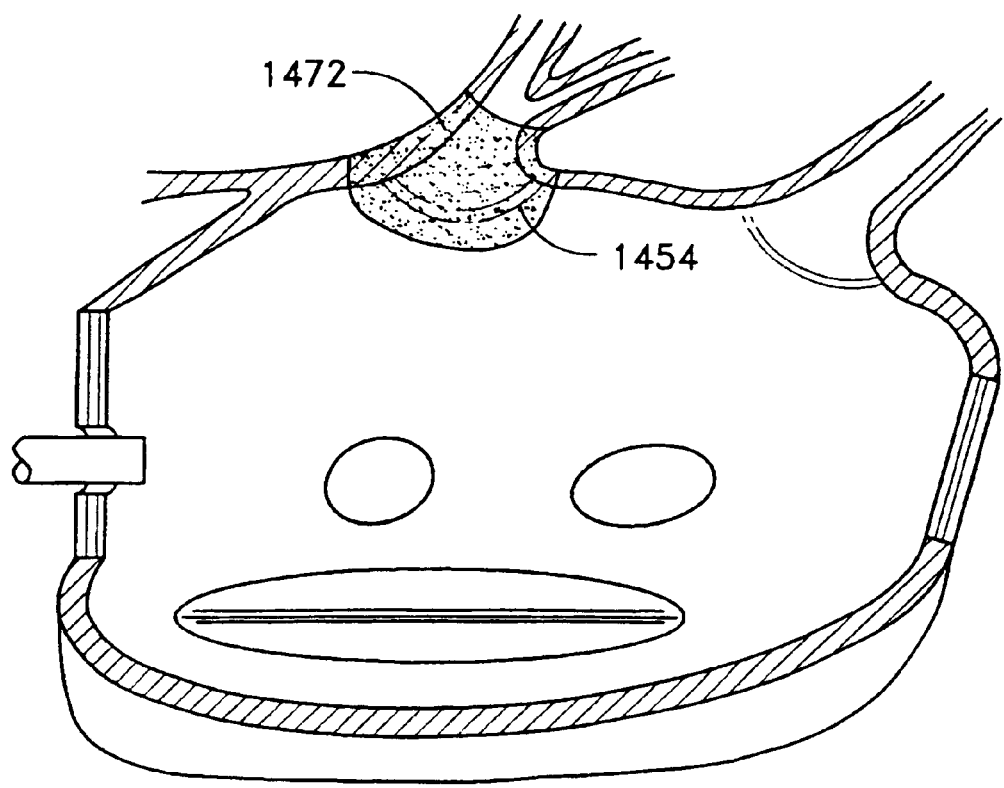
FIG. 14C shows a sectional view of a circumferential conduction block in a pulmonary vein as formed by a circumferential ablation device such as according to the modes shown in FIGS. 14A–B.

FIGS. 14A–B show a further variation in another embodiment of the present invention, wherein a circumferential ablation member (1450) includes a radially compliant expandable member (1470) which is adapted to conform to a pulmonary vein ostium (1454) at least in part by adjusting it to a radially expanded position while in the left atrium and then advancing it into the ostium. FIG. 14A shows expandable member (1470) after being adjusted to a radially expanded position while located in the left atrium (1450). FIG. 14B further shows expandable member (1470) after being advanced into the pulmonary vein (1451) until at least a portion of the expanded working length L of circumferential ablation member (1450), which includes a circumferential band (1452), engages the pulmonary vein ostium (1454). FIG. 14C shows a portion of a circumferential lesion (1472) which forms a circumferential conduction block in the region of the pulmonary vein ostium (1454) subsequent to actuating the circumferential ablation element to form the circumferential lesion.

In addition to conforming to the pulmonary vein ostium, expandable member (1470) is also shown in FIG. 14B to engage a circumferential path of tissue along the left posterior atrial wall that surrounds ostium (1454). Moreover, circumferential band (1452) of the circumferential ablation member is also thereby adapted to engage that atrial wall tissue. Therefore, the circumferential conduction block formed according to the method shown and just described in sequential steps by reference to FIGS. 14A–B, as shown in-part in FIG. 14C, includes ablating the circumferential path of atrial wall tissue which surrounds ostium (1454). Accordingly, the entire pulmonary vein, including the ostium, is thereby electrically isolated from at least a substantial portion of the left atrial wall which includes the other of the pulmonary vein ostia, as would be apparent to one of ordinary skill according to the sequential method steps shown in FIGS. 14A–B and by further reference to the resulting circumferential lesion (1472) shown in FIG. 14C.

The lesion shown in FIG. 14C isolates the pulmonary vein, but is formed by ablating tissue surrounding the pulmonary vein, although while also within the pulmonary vein. It is further contemplated that such lesion may be formed only along the posterior left atrial wall and surrounding the pulmonary vein ostium, without also ablating tissue along the lumen or lining of the pulmonary vein or ostium, depending upon the particular shape of the balloon and/or position and geometry of the ablative band along that balloon. In one aspect of this embodiment, the compliant nature of the expandable member may be self-conforming to the region of the ostium such that the circumferential band is placed against this atrial wall tissue merely by way of conformability.

According to a further example, a pear-shaped balloon with a distally reducing outer diameter may provide a "forward-looking" face which, with the ablative band provided along that forward-looking face, is adapted to advance against such atrial wall tissue and ablate there. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band of the ablation member is preferably placed along the surface of the contoured taper which is adapted to face the left posterior atrial wall during use, such as for example according to the method illustrated by FIGS. 14A–B.

Figure 15C:
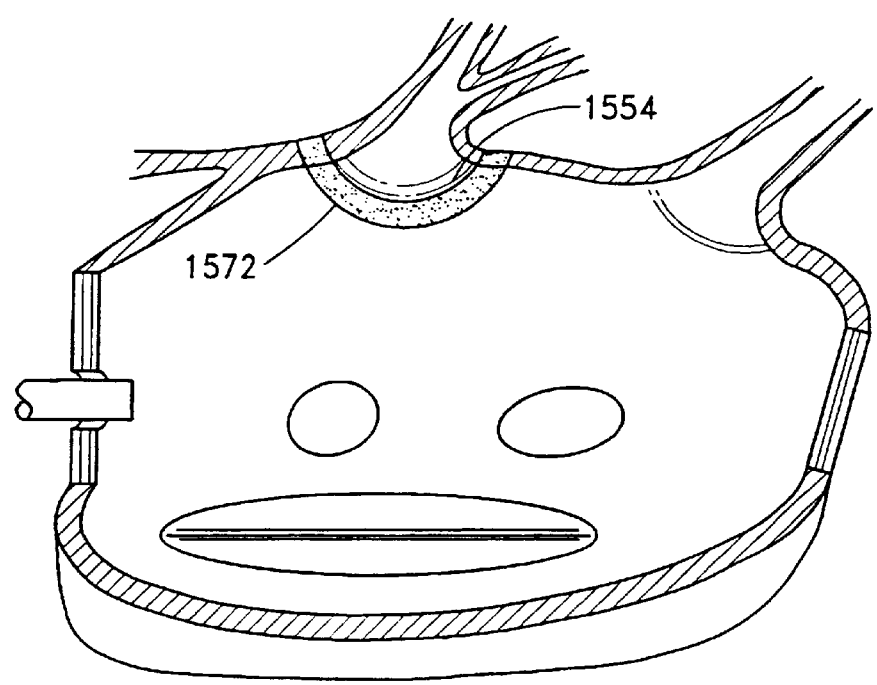
FIG. 15C shows a sectioned perspective view of a circumferential conduction block formed according to the method and device shown in FIGS. 15A–B along the posterior left atrial wall and surrounding the pulmonary vein ostium.

FIGS. 15A–C show such a pear-shaped ablation balloon in a circumferential ablation member assembly adapted to electrically isolate a pulmonary vein and ostium from a substantial portion of the left posterior atrial wall, which embodiment isolates the pulmonary vein without also ablating tissue along the lumen or lining of the pulmonary vein or ostium.

In more detail, FIG. 15A shows circumferential band (1552') to have a geometry (primarily width) and position along expandable member (1570') such that it is adapted to engage only a circumferential path of tissue along the left posterior atrial wall which surrounds the pulmonary vein ostium. In one aspect of this embodiment, the compliant nature of the expandable member may be self-conforming to the region of the ostium such that the circumferential band is placed against this atrial wall tissue merely by way of conformability.

In another variation, a "pear"-shaped expandable member or balloon that includes a contoured taper may be suitable for use according to the FIG. 15A embodiment, as is shown by way of example in FIG. 15B. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band (1552') of the ablation member is preferably placed along the surface of the contoured taper which is adapted to face the left posterior atrial wall during use according to the method illustrated by FIG. 15A. It is further contemplated that the ablation element may be further extended or alternatively positioned along other portions of the taper, such as is shown by example in shadow at extended band (1552") in FIG. 15B. Accordingly, the variation shown in FIG. 15B to include extended band (1552") may also adapt this particular device embodiment for use in forming circumferential conduction blocks also along tissue within the pulmonary vein and ostium, such as according to the previously described method shown in FIGS. 15A–C.

The tissue ablation device systems shown and described below by reference to FIGS. 16A–21 are also believed to be beneficial for ablating tissue at certain locations where one or more pulmonary veins extend from an atrium.

Figures 16A, 16B:
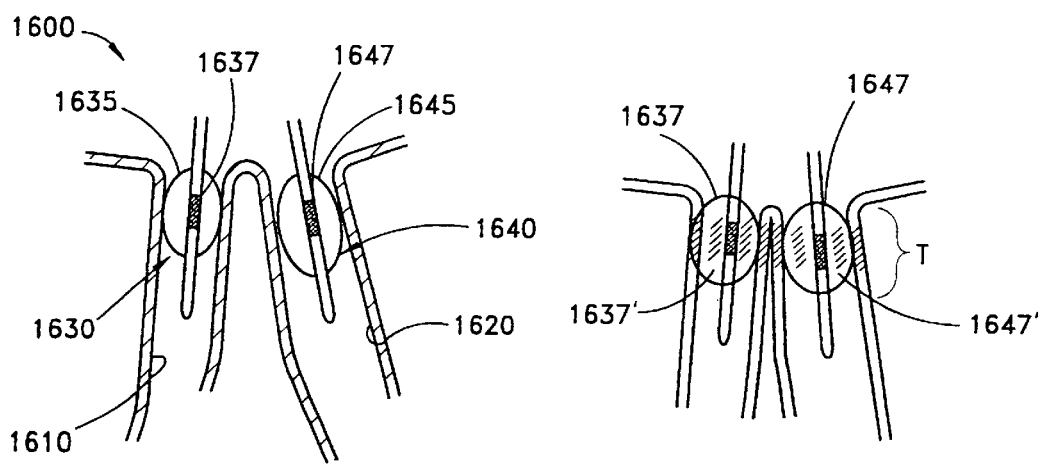
FIGS. 16A–B show sequential modes of use of a dual-ablation balloon system for ablating two circumferential regions of tissue at two locations, respectively, where two adjacent pulmonary vein branches, also respectively, extend from an atrial wall.

The tissue ablation device system (1600) shown in FIGS. 16A–B includes two circumferential ablation devices (1630, 1640) in two pulmonary vein branches (1610,1620) which form adjacent ostia along an atrial wall. Each of devices (1630,1640) has a circumferential ablation member (1632, 1642), respectively, which is shown to include an expandable member (1635,1645), also respectively, and an ablative energy source (1637,1647), also respectively. Each respective ablative energy source (1637,1647) is adapted to ablatively couple to a circumferential region of tissue at the base of the respective pulmonary vein (1610,1620), and if properly positioned, may combine to ablate tissue between the adjacent veins (1610,1620), as shown specifically in FIG. 16B wherein the expandable members expand the veins (1610,1620) to bring them together to assist the combined ablative coupling from each device to the tissue therebetween.

Figure 17:
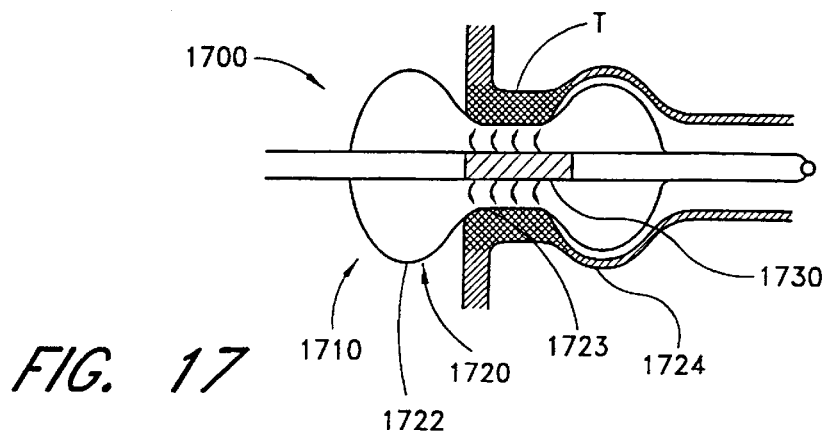
FIG. 17 shows a further shape for an expandable member according to the tissue ablation devices and procedures according to the invention.

Pulmonary veins have also been observed to present a thickened cuff of tissue at their respective ostia, which thickened cuff is believed to present a unique resistance to expansion of an expandable member with a working length extending from the atrium, across the ostia, and into the more compliant vein adjacent the ostium. Therefore, one embodiment of the invention further contemplates an expandable balloon having a shape with a waist which assists the balloon to seat at the thickened, less compliant ostium and position the ablative circumferential band of the ablation assembly there. Such an embodiment is shown in FIG. 17, wherein device (1700) is shown with a circumferential ablation member (1710) having an expandable member (1720) that is a balloon with a narrowed waist (1723) between two larger end portions (1720,1724) of the working length. As shown, distal end portion (1724) of the balloon's working length expands with the vein wall, and proximal end portion (1720) of the balloon's working length expands to a relatively large outer diameter as the ostium becomes atrium. However, waist (1723) with its reduced diameter allows the assembly to seat at the thicker ostium with ablation element (1730) well positioned to ablatively couple through expandable member (1720) and into the circumferential region of tissue along the ostium, such as for example according to the balloon embodiments with a permeable circumferential band as described above.

Various particular material constructions may be used for a balloon such as just described for FIG. 17, in addition to particular ablation element/expandable member configurations, and still benefit by the "peanut" or waisted balloon shape with regards to pulmonary vein ostium ablation. In particular with regards to material construction, either a substantially compliant or elastomeric balloon material, or a substantially non-compliant or non-elastomeric variety may be used. Or, a combination balloon construction with elastomeric/compliant and non-elastomeric/non-compliant regions along the working length, such as herein described, may be suitable.

Figure 18:
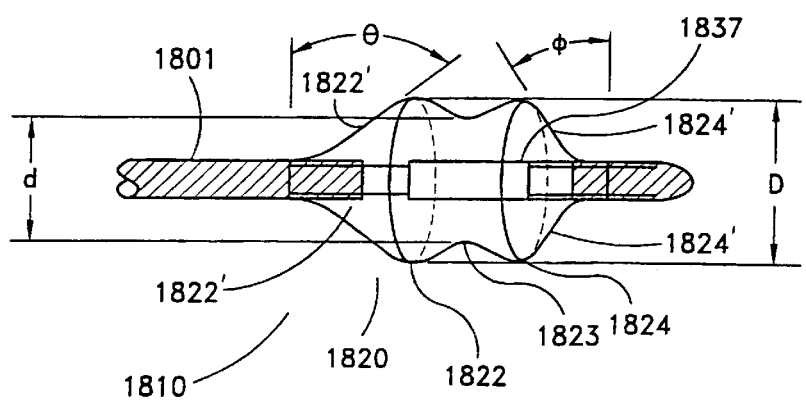
FIG. 18 shows a further shape for an expandable member according to the invention.

In addition, various modifications of the respective sizes and dimensions for the end portions and reduced diameter intermediate waist region are also contemplated. For example, FIG. 18 shows a further iteration of a "waisted" balloon shape for circumferential ablation member (1810), and in particular shows distal shoulder (1824) of expandable member or balloon (1820) having a steeper angled taper (1824') onto the distal adaption to the underlying catheter body (1801) than is shown for taper (1822') between catheter body (1801) and proximal shoulder (1822). This illustrates that the dimensions at the distal most portion of the assembly may be desirably as blunt as possible, whereas certain pulmonary veins have been observed to quickly branch or otherwise narrow in close proximity to the ostium and thereby prevent the distal end of the ablation device to be advanced very far through the respective ostium for ablation. Thus, the steeper distal taper (1824') allows the waist region (1823), including in various particular embodiments the ablative circumferential band coupled to the ablation element (1837), to be placed as distally as possible on the underlying catheter body (1801) to ensure the ability to ablate the ostium.

FIGS. 19A–21 show various uses of multiple expansion elements in order to assist in the proper positioning of the ablation element and respective expandable member for ablative coupling to a circumferential region of tissue where a pulmonary vein extends from an atrium.

More particularly, FIG. 19A shows a circumferential ablation member (1900) with an expandable member (1910) and an ablation element (1940). Expandable member (1910) includes an outer tubular wall (1912) which surrounds each of two spaced inner expansion elements (1920,1930). According to this configuration, inner expansion elements (1920,1930) are located along first and second end portions a,c of the working length L of expandable member (1910).

The proximal inner expansion element (1920) is shown in FIG. 19A as a balloon which is fluidly coupled to a source of inflation fluid via port (1922), whereas distal inner expansion element (1930) is also shown as a balloon and is fluidly coupled to a source of inflation fluid via port (1932). Proximal inner expansion element (1920) is adapted to expand to a larger outer diameter D than the outer diameter d for distal expansion element (1930), and thereby the overall expandable member (1910) results in an overall tapered shape and in particular imparting a taper with a distally reducing outer diameter along tubular wall (1912) extending between the different diameter expansion elements (1920,1930).

Moreover, the spacing between expansion elements (1920,1930) defines an intermediate region b wherein an interior chamber (1915) is enclosed by outer tube (1912) extending between the expansion elements (1920,1930). Interior chamber (1915) is adapted to be fluidly coupled to a source of ablative medium (not shown) via port (1917) into a fluid passageway (also not shown) extending along elongate body (1901). An ablation element (1940) is provided on elongate body (1901) between expansion elements (1920, 1930) and within interior chamber (1915), and is adapted to be coupled to an ablation actuator along a proximal end portion (not shown) of body (1901).

As inflation of both proximal and distal inner expansion elements (1920,1930) causes the overall expandable member (1910) to take on the tapered shape as shown in FIG. 19A, chamber (1915) is filled with an ablative coupling medium through port (1917). In use, such as shown in FIGS. 19B–C, this assembly is positioned such that an ablative circumferential band along intermediate region b is engaged to the circumferential region of tissue at the location where a pulmonary vein extends from an atrium. The expandable member (1910) may be expanded to the tapered configuration prior to delivery into the pulmonary vein ostium, as shown in the particular modes of FIGS. 19B–C, or delivered to the desired location and then expanded variously along the different regions of the working length as described. In the prior instance, the large outer diameter D along proximal end portion c may be ideally sized to abut the vein ostium and remain at least partially within the atrium, whereas the circumferential ablative coupling along intermediate region b is distal thereto and ensured to be at the ostium and below the conduction from an arrhythmogenic focus along the vein.

It may not be necessary in some instances however to have both of two inner expansion elements such as just described by reference to FIGS. 19A–C and still achieve the desired shaped expansion member, as is illustrated by the circumferential ablation member (2000) shown in FIG. 20. Circumferential ablation member (2000) includes an outer tube (2012) that encloses a proximal inner expansion element (2020) in a similar manner to that shown in FIG. 19A. However, the distal end portion a of the FIG. 20 embodiment does not require the presence of the second, distal inner expansion element. Rather, outer tube (2012) terminates distally on to shaft (2001) such that chamber (2015) is formed within outer tube (2012) everywhere distally of proximal inner expansion element (2020). Fluid is infused through port (2017) in order to inflate outer tube (2012) to the desired outer diameter along both distal end portion c and intermediate region b. By expanding proximal expansion element (2020) to a higher pressure than that provided within interior chamber (2015), proximal end portion a thus expands to the greater diameter D to impart the overall stepped or tapering shape and in some applications to provide the "stop" at the ostium in order to position the ablation element as desired for ostial ablation.

Two spaced expansion elements of distally reducing outer diameters, such as the two elements described for FIGS. 19A–C, may also provide a beneficial overall ablation assembly without the need to enclose an ablative chamber between those elements as specifically shown in FIG. 19. For example, FIG. 21 shows a circumferential ablation member (2100) that includes an expandable member (2110) that includes a circumferential ablation element assembly as previously described above. However, FIG. 21 also provides a second expandable member (2120) positioned proximally of expandable member (2110) along shaft (2101), and which has a larger outer diameter D than the outer diameter d of expandable member (2110). However, distal expandable member (2130) also includes and an ablation element within the first expandable member.

Further to the method for using the circumferential ablation device assembly of the present invention, electrical signals along the pulmonary vein may be monitored with a sensing element before and after ablation. Signals within the pulmonary vein are monitored prior to forming a conduction block, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself.

The circumferential ablation members providing an ablative circumferential band along an expandable balloon, according to the various embodiments described herein, can also include additional mechanisms to control the depth of heating. For instance, the elongate body associated with delivering an RF ablation member embodiment to the left atrium and pulmonary vein can include an additional lumen which is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon can thus act as a heat sink to conduct away some of the heat from the targeted tissue and maintain the tissue below a desired temperature (e.g., 90 degrees C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

Various of the device assemblies herein disclosed which provide an ablation balloon with an ablative circumferential band, in addition to the related methods of manufacture and use, are also considered applicable to modes other than the porous electrode type ablation element mode specifically described, such as for example by reference to FIGS. 5A–11D. For example, a band of thermally conductive material may be used in replacement of a porous material along the intermediate region of the balloon construction in order to form a thermal ablation element, and such features are considered useful with various of the disclosed embodiments such as for example with regard to the disclosed assemblies with elastomeric material only along the end portions of the working length, shapes for the respective expandable member having reduced diameter waists and/or tapers, etc. Moreover, the varied construction between the intermediate region and the end portions of the balloon according to those embodiments may also be applicable to an ultrasound ablation member, for example by varying the materials between these portions based upon their ultrasonically transmissive character, or for other purposes such as otherwise herein described.

In the case of the contemplated radiofrequency ("RF") ablation variations for the various embodiments using an electrode within an expandable member or balloon, an ablation actuator is connected to the electrode and also to a ground patch. A circuit thereby is created which includes the ablation actuator, the ablation member, the patient's body, and the ground patch that provides either earth ground or floating ground to the current source. In the circuit, an electrical current, such as a radiofrequency ("RF") signal may be sent through the patient between the ablation member and the ground patch, as well known in the art.

At least one conductor lead connects to the electrode when provided within a balloon to form a circumferential ablation member assembly. A suitable conductor lead is a 36 AWG copper wire insulated with a 0.0005 inch thick polyimide coating. A distal end of the lead is exposed and is electrically coupled to the electrode. The corresponding conductor lead wire is soldered to the coil with a 95 Ag/5 Sn. The conductor wire can also be electrically connected to the electrode by other means, such as, for example, by resistant, ultrasonic or laser welding. In addition, the coil and the conductor can be unitary by winding the distal end of the conductor in a helical pattern. The proximal end of each conductor lead is connected to an electrical connector on the proximal end of the tissue ablation device assembly for coupling to a current source.

Exemplary porous materials suitable for use according to various of the embodiments above include porous fluoropolymers such as expanded polytetrafluoroethylene (PTFE), porous polyethylene, porous silicone, porous urethane, and tightly weaved matrices such as of dacron. Such porous materials are formed using conventional techniques, such as, for example by blowing the material or by drilling micro holes within the material. One range of porosity which is believed to be suitable is between about 5 and 50 microns. A specific type of porous PTFE material that is believed to be suitable is available commercially from International Polymer Engineering, of Tempe, Ariz., as Product Code 014-03. It has been found that fluid will pass through this material upon applying a relatively low pressure within the material (e.g., 5 psi).

Examples of suitable electrodes and electrode lead configurations for use according to the RF ablation variations of the disclosed embodiments, in addition to various aspects of fluid permeable membranes for use in fluid coupled electrode assemblies as referenced above, are disclosed in copending U.S. patent application Ser. No. 09/073,907 for "Tissue Ablation Device with Fluid Irrigated Electrode", to Alan Schaer et al., filed May 6, 1998, which is herein incorporated in its entirety by reference thereto.

One suitable electrode configuration for use in the illustrated embodiments comprises a wire coil formed in a helical pattern. Such a coil electrode desirably has a sufficiently large inner diameter to receive the inner member or support tubings while its outer diameter is sized to provide sufficient mass for necessary current emission during ablation, though limited by the need to delivery the device within reasonable delivery catheters such as in a transeptal procedure. In one more specific mode believed to be suitable, the electrode comprises a 0.005 inch diameter wire made of a biocompatible material (e.g., stainless steel, platinum, gold-plated titanium alloy, etc.). The wire is unshielded and is wound in a helical fashion with about a 0.048 inch inner diameter. The coils are spaced along the length of the tubing that extends longitudinally through the ablation balloon with the porous membrane. In a further specific mode, the electrode coil has a length, as measured in the longitudinal direction, of about 0.28 inch or more.

The electrode of the ablation member desirably has sufficient flexibility to bend to track through a venous or arterial access path to an ablation target site. The coil construction just illustrated provides such flexibility. The electrode can, however, have other configurations that also afford similar flexibility. For instance, the electrode can have a tubular or cylindrical shape formed by a plurality of braided wires. End bands may link the ends of the wires together to prevent the braided structure from unraveling. The end bands can also electrically couple the wires together. The bands though are sufficiently narrow so as not to meaningfully degrade the flexibility of the ablation element. Any braided pattern can work, but a "diamond" pattern mesh is preferred. The wires of the braid can either have rectangular ("flat") or rounded cross sections. The wire material can be any of a wide variety of known biocompatible materials (such as those identified above in connection with the coil electrodes). In one mode, the braided electrode can be "wound" before inserting into the tubular porous membrane. Once inserted, the electrode can be uncoiled to press against the inner surface of the tube. In this manner, the membrane can support the electrode.

Another electrode construction is formed from a flat wire mesh that has been rolled into an arcuate structure. The structure has a semi-cylindrical shape; however, the structure can extend through either more or less of an arc. Another suitable electrode has a "fishbone" pattern. This electrode includes a plurality of arcuate segments that extend from an elongated section which generally lie parallel to a longitudinal axis of the ablation member when assembled. The ends of each arcuate segment can be squared (as illustrated) or rounded. Another suitable electrode is formed in an "arches" pattern. A plurality of arch segments lie in series with two side rails interconnecting the corresponding ends of the arch segments. The arch segments are spaced apart from one another along the length of the electrode. Etching or laser cutting a tube of electrode material can form such electrode configurations as just described.

Common to all of the illustrated electrodes is the ability to flex, though such feature is not mandatory according to the overall invention. The flexibility of these electrodes allows them to bend through tight turns in the venous or arterial access path without collapsing. The electrodes also have low profiles so as to minimize the outer diameter of the overall ablation device assembly. Fluid also can pass radially through the electrodes in some further embodiments not shown. Other types of electrode designs that exhibit these features can also be used. For example, the electrode can be formed in a manner resembling a conventional stent by etching or laser cutting a tube. The electrode also need not extend entirely about the longitudinal axis of the ablation member; the electrode can be generally flat and positioned on only one side of the catheter. A serpentine shape would provide such a flat electrode with the desired flexibility. Accordingly, the foregoing electrode designs are merely exemplary of the types of electrodes that can be used with the present ablation member.

The tissue ablation device assemblies of the invention also may include feedback control. For instance, one or more thermal sensors (e.g., thermocouples, thermisters, etc.) may be provided with the circumferential ablation device assemblies described, such as either on the outer side or the inside of the porous circumferential band for instance. Monitoring temperature at this location provides indicia for the progression of the lesion. The number of thermocouples may be determined by the size of the circumference to be ablated. If the temperature sensors are located inside the porous membrane, the feedback control may also need to account for any temperature gradient that occurs across the membrane. Furthermore, sensors placed on the exterior of the porous member may also be used to record electrogram signals by reconnecting the signal leads to different input port of the signal processing unit. Such signals can be useful in mapping the target tissue both before and after ablation.

In one embodiment, the temperature sensors comprise a thermocouple that is positioned about the outer side of the porous membrane along the circumferential band. In this location, the thermocouple lies on the outside of the band where it can directly contact the tissue-electrode interface. The thermocouples may also be blended into the outer surface of the ablation balloon in order to present a smooth profile. Transition regions which may be formed by either adhesive or melted polymer tubing, "smooth out" the surface of the ablation member as the surface steps up from the porous member outer surface to the thermocouple surface. Signal wires generally extend from the thermocouples to an electrical connector on the proximal end of the circumferential tissue ablation device assembly. The wires may be shielded. The thermocouple wires may extend along the catheter shaft longitudinally in a dedicated or shared lumen, or the wires can form a braided structure extending along the elongated body. The wires can also be routed proximally inside one or more tubes that extend parallel to and are attached to the elongated body. The wires can also be sewn into the wall along the circumferential band. These represent a few variations on various ways of routing the thermocouple wires to the proximal end of the tissue ablation device assembly.

Other feedback sensors and related assemblies, including for sensing ablation progression as well as position monitoring sensors and systems, are specifically contemplated in combination with the embodiments of this disclosure, including the various embodiments disclosed in copending U.S. Provisional Application Serial No. 60/122,571, which is incorporated by reference below.

It is further contemplated that the embodiments shown and described herein may be combined, assembled together, or where appropriate substituted for, the various features and embodiments which are disclosed in the following co-pending provisional and non-provisional U.S. Patent Applications: the co-pending non-provisional U.S. Patent Application for "FEEDBACK APPARATUS AND METHOD FOR ABLATION AT PULMONARY VEIN OSTIUM", filed on Nov. 5, 1999, and claiming priority to Provisional U.S. Patent Application No. 60/122,571, filed on Mar. 2, 1999; co-pending U.S. patent application Ser. No. 09/569,735 for "BALLOON ANCHOR WIRE", filed May 11, 2000, and claiming priority to Provisional Application No. 60/133,610 filed May 11, 1999; co-pending non-provisional U.S. Patent Application Ser. No. 09/435,281 for "TISSUE ABLATION DEVICE ASSEMBLY AND METHOD FOR ELECTRICALLY ISOLATING A PULMONARY VEIN OSTIUM FROM A POSTERIOR LEFT ATRIAL WALL", filed on Nov. 5, 1999, and which claims priority to Provisional U.S. Patent Application No. 60/133,677, filed May 11, 1999; the co-pending non-provisional U.S. patent application Ser. No. 09/435,280 for "APPARATUS AND METHOD INCORPORATING AN ULTRASOUND TRANSDUCER ONTO A DELIVERY MEMBER", filed on Nov. 5, 1999, and which claims priority to Provisional U.S. Patent Application No. 60/133,680, filed May 11, 1999; and co-pending Provisional U.S. Patent Application Serial No. 60/133,807 for "CATHETER POSITIONING SYSTEM". The disclosures of these references are herein incorporated in their entirety by reference thereto.

In addition, a circumferential ablation device assembly according to the present invention may be used in combination with other linear ablation assemblies and methods, and various related components or steps of such assemblies or methods, respectively, in order to form a circumferential conduction block adjunctively to the formation of long linear lesions, such as in a less-invasive "maze"-type procedure. Examples of such assemblies and methods related to linear lesion formation and which are contemplated in combination with the presently disclosed embodiments are shown and described in the following additional U.S. Patent Applications and Patents: U.S. Pat. No. 5,971,983, issued on Oct. 26, 1999, entitled "TISSUE ABLATION DEVICE AND METHOD OF USE" filed by Michael Lesh, M.D. on May 9, 1997; U.S. Ser. No. 09/260,316 for "TISSUE ABLATION SYSTEM AND METHOD FOR FORMING LONG LINEAR LESION" to Langberg et al., filed May 1, 1999; co-pending U.S. Application entitled "TISSUE ABLATION SYSTEM AND METHOD FOR FORMING LONG LINEAR LESIONS," to Langberg et al., filed Feb. 25, 2002; and U.S. Ser. No. 09/073,907 for "TISSUE ABLATION DEVICE WITH FLUID IRRIGATED ELECTRODE", to Alan Schaer et al., filed May 6, 1998. The disclosures of these references are herein incorporated in their entirety by reference thereto.

Other additional variations or modifications of the present embodiments that are not themselves specifically herein disclosed may be made by one of ordinary skill without departing from the scope of the present invention. For example, obvious variations or modifications to the detailed embodiments herein shown or described, including for example various combinations or sub-combinations among features of the detailed embodiments, may be made by one of ordinary skill based upon this disclosure and remain within the scope of the invention.

What is claimed is:

1. A tissue ablation device assembly, comprising:

an elongate catheter body with a proximal end portion and a distal end portion;

an expandable member mounted along said distal end portion of said elongate catheter body and defining an interior chamber, said expandable member having an exterior surface adapted for engagement with a region of tissue when in an expanded condition, said expandable member being formed at least in part with a porous membrane;

first and second expansion elements coupled to said expandable member for expanding said expandable member;

an ablation element disposed within said interior chamber, said ablation element being shaped for emitting ablative energy through said expandable member for ablating at least a portion of the region of tissue; and a fluid passageway extending through said elongate catheter body and communicating with said interior chamber, said fluid passageway being adapted to be fluidly coupled to a fluid source for delivering a volume of ablative medium from said fluid source to said interior chamber, wherein said ablative medium is allowed to pass through said porous membrane for ablatively coupling said ablation element to the region of tissue.

2. The tissue ablation device assembly of claim 1, wherein said first and second expansion elements are capable of providing said expandable member with a tapered shape.

3. The tissue ablation device assembly of claim 2, wherein said expandable member has a reducing diameter in the distal direction when in said expanded condition.

4. The tissue ablation device assembly of claim 1, wherein said first and second expansion elements are fluidly coupled to a fluid source.

5. The tissue ablation device assembly of claim 1, wherein said ablation element is an ultrasound transducer.

6. The tissue ablation device assembly of claim 1, wherein said ablative medium fills a central region of said interior chamber between said first and second expansion elements.

7. The tissue ablation device assembly of claim 1, wherein said porous membrane forms a permeable band along said expandable member.

8. The tissue ablation device assembly of claim 1, wherein said expandable member is adapted for engagement with a circumferential region of tissue when in said expanded condition.

9. The tissue ablation device assembly of claim 1, wherein said first and second expansion elements are located within said interior chamber of said expandable member.

10. The tissue ablation device assembly of claim 9, wherein said first and second expansion elements are inflatable elements provided at proximal and distal ends of said interior chamber.

11. The tissue ablation device assembly of claim 10, wherein said interior chamber of said expandable member is configured to be filled with an ablative medium in a region between said first and second inflatable elements.

12. A tissue ablation device assembly, comprising:

an elongate catheter body with a proximal end portion and a distal end portion, said elongate catheter body defining a fluid passageway;

an expandable member mounted along said distal end portion of said elongate catheter body and defining an interior chamber in fluid communication with said fluid passageway, said expandable member being formed with a permeable band adapted for engagement with a region of tissue when in an expanded condition;

a first expansion element disposed at a proximal end of said expandable member;

a second expansion element disposed at a distal end of said expandable member; and an ablation element disposed within said interior chamber of said expandable member between said first and second expansion elements;

wherein said first and second expansion elements are inflatable for increasing a diameter of said expandable member for engagement with the region of tissue and wherein an ablative medium is deliverable into said interior chamber and out through said permeable band for ablatively coupling said ablation element to the region of tissue.

* * * * *